(12) United States Patent
Eckstein et al.

(10) Patent No.: US 7,731,815 B2
(45) Date of Patent: Jun. 8, 2010

(54) METHOD AND APPARATUS FOR NONLINEAR LAYING OF MATERIAL

(75) Inventors: Joseph A. Eckstein, Sunman, IN (US); Bradley E. Walsh, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 819 days.

(21) Appl. No.: 11/593,361

(22) Filed: Nov. 6, 2006

(65) Prior Publication Data

US 2008/0105384 A1    May 8, 2008

(51) Int. Cl.
*B32B 37/00*    (2006.01)
*A61F 13/15*    (2006.01)

(52) U.S. Cl. .................. 156/161; 156/163; 156/164; 156/229; 156/494; 156/495; 156/496

(58) Field of Classification Search .................. 156/160, 156/161, 163, 164, 229, 494–496
See application file for complete search history.

(56) References Cited

U.S. PATENT DOCUMENTS

| | | | |
|---|---|---|---|
| 2,630,773 A * | 3/1953 | Caprara | 112/470.31 |
| 3,860,003 A | 1/1975 | Buell | |
| 4,081,301 A | 3/1978 | Buell | |
| 4,293,367 A | 10/1981 | Klasek et al. | |
| 4,479,836 A | 10/1984 | Dickover et al. | |
| 4,515,595 A | 5/1985 | Kievit et al. | |
| 4,573,986 A | 3/1986 | Minetola et al. | |
| 4,675,068 A * | 6/1987 | Lundmark | 156/495 |
| 4,801,345 A | 1/1989 | Dussaud et al. | |
| 4,842,666 A | 6/1989 | Werenicz | |
| 4,915,767 A | 4/1990 | Rajala et al. | |
| 4,917,746 A | 4/1990 | Kons et al. | |
| 5,236,539 A * | 8/1993 | Rogberg et al. | 156/495 |
| 5,500,075 A | 3/1996 | Herrmann | |
| 5,525,175 A | 6/1996 | Blenke et al. | |
| 5,660,664 A | 8/1997 | Herrmann | |
| 6,284,081 B1 | 9/2001 | Vogt et al. | |
| 6,287,409 B1 | 9/2001 | Stephany | |
| 6,585,841 B1 | 7/2003 | Popp et al. | |
| 6,610,161 B2 | 8/2003 | Erdman | |
| 2002/0084018 A1 | 7/2002 | Ward et al. | |

FOREIGN PATENT DOCUMENTS

| | | |
|---|---|---|
| EP | 1260203 A2 | 11/2002 |
| GB | 2123272 A | 2/1984 |
| JP | 09-295754 A * | 11/1997 |
| JP | 11332913 | 12/1999 |

\* cited by examiner

*Primary Examiner*—Jeff H Aftergut
(74) *Attorney, Agent, or Firm*—Charles R. Ware

(57) ABSTRACT

A method and apparatus for nonlinear laying of components such as elastics on a continuous web is provided. In an apparatus embodiment, the apparatus comprises a diverter and a combining roll. The apparatus can be configured to vary an elastic profile of the elastic member on a continuous web by oscillating a rotation of the diverter. The method and apparatus can be used for making absorbent articles such as diapers and training pants.

32 Claims, 29 Drawing Sheets

METHOD AND APPARATUS FOR NONLINEAR LAYING OF MATERIAL

FIELD OF THE INVENTION

The present invention relates to a method for making absorbent articles such as diapers and training pants. More particularly, the present invention relates to a method and apparatus for nonlinear laying of components such as elastics on a diaper.

BACKGROUND OF THE INVENTION

Diapers for absorbing exudates from a wearer are known. It is common to provide such diapers with elastic along side edges of a diaper to cause the diaper to contract around leg openings to fit the diaper around the legs of a wearer. Typically, these diapers have absorption pads or bodies of an hour-glass or similar configuration, in which the narrower center part, intended to conform to the shape of the body, forms the crotch part of the diaper when the diaper is in use. Elastic members positioned generally rectilinearly and generally parallel with the longitudinal axis of the diaper tend to result in chafing of the skin of the wearer in the crotch region. Because of this and because the leg openings in the diaper typically are curved, it is desirable to lay the elastic members in a curved elastic profile that is generally parallel to the side edges of the diaper. Thus, at least a portion of the elastic profile typically is curved to match the curvature of the side edges along the leg openings. It would be advantageous to lay components such as elastics in a nonlinear fashion during manufacturing of an absorbent article that may easily be customized for different elastic profiles.

SUMMARY OF THE INVENTION

A method and apparatus for nonlinear laying of components such as elastics on a continuous web is provided.

In one embodiment, the apparatus comprises a diverter and a combining roll. The diverter has a groove and an axis of rotation, the groove having a pitch corresponding to an axial length of travel of the groove as it wraps once around an outer surface of the diverter. The groove is configured for receiving the elastic member and directing the elastic member out of an exit point of the groove. The diverter is configured for oscillating rotation, wherein rotation of the diverter moves the exit point in a cross machine direction. The combining roll has an axis of rotation and is configured for receiving the elastic member from the diverter and combining the elastic member with the continuous web. The axis of rotation of the diverter is positioned at an angle relative to the axis of rotation of the combining roll such that an elastic member travels from the exit point of the groove of the diverter to the combining roll on a path that is generally perpendicular to the axis of rotation of the combining roll. Using the apparatus, an elastic profile of the elastic member on the continuous web may be varied by oscillating a rotation of the diverter.

In another embodiment, the apparatus comprises a diverter, a combining roll, a first positioning member, a second positioning member, and a third positioning member. The diverter has a groove and an axis of rotation, the groove having a pitch corresponding to an axial length of travel of the groove as it wraps once around an outer surface of the diverter. The groove is configured for receiving the elastic member and directing the elastic member out of an exit point of the groove. The diverter is configured for oscillating rotation, wherein rotation of the diverter moves the exit point in a cross machine direction. The combining roll has an axis of rotation and is configured for receiving the elastic member from the diverter and combining the elastic member with the continuous web. The first positioning member is positioned upstream of the diverter and holds the elastic member in a first orientation. The second positioning member is positioned between the first positioning member and the diverter and orients the elastic member to generally correspond with orientation of the groove. The third positioning member is positioned between the diverter and the combining roll and orients the elastic member to generally correspond with the orientation of the continuous web. The axis of rotation of the diverter is positioned at an angle relative to the axis of rotation of the combining roll such that an elastic member travels from the exit point of the groove of the diverter to the combining roll on a path that is generally perpendicular to the axis of rotation of the combining roll. Using the apparatus, an elastic profile of the elastic member on the continuous web may be varied by oscillating a rotation of the diverter.

In yet a further embodiment, the apparatus comprises a generally conical diverter and a combining roll. The diverter has a groove and an axis of rotation, the groove having a pitch corresponding to an axial length of travel of the groove as it wraps once around an outer surface of the diverter. The groove is configured for receiving the elastic member and directing the elastic member out of an exit point of the groove. The diverter is configured for oscillating rotation, wherein rotation of the diverter moves the exit point in a cross machine direction. The combining roll has an axis of rotation and is configured for receiving the elastic member from the diverter and combining the elastic member with the continuous web. The axis of rotation of the diverter is positioned at a generally nonparallel angle relative to the axis of rotation of the combining roll such that an elastic member travels from the exit point of the groove of the diverter to the combining roll on a path that is generally perpendicular to the axis of rotation of the combining roll and wherein an outer surface of the generally conical diverter is generally parallel to an outer surface of the combining roll. Using the apparatus, an elastic profile of the elastic member may be varied by oscillating a rotation of the diverter.

In accordance with a further embodiment, the method comprises providing a diverter, providing a combining roll, directing the elastic member into a groove of the diverter, oscillating a rotation of the diverter, directing the elastic member to the combining roll, and combining the elastic member with the continuous web. Providing a diverter comprises providing a diverter having a groove and an axis of rotation. The groove has a pitch corresponding to an axial length of the groove as it wraps once around an outer surface of the diverter. The groove is configured for receiving the elastic member and for directing the elastic member out of an exit point of the groove. The diverter is configured for oscillating rotation, wherein rotation of the diverter moves the exit point in a cross machine direction. Providing a combining roll comprises providing a combining roll having an axis of rotation. The combining roll is configured for receiving the elastic member from the diverter and combining the elastic member with the continuous web. Directing the elastic member comprises directing the elastic member into the groove. Oscillating the rotation of the diverter comprises oscillating a rotation of the diverter to move the exit point in a cross machine direction while feeding the elastic member through the groove. Directing the elastic member to the combining roll comprises directing the elastic member from the exit point to the combining roll on a path that is generally perpendicular to the axis of rotation of the combining roll. Combining the elastic member with the continuous web comprises combining the elastic member with the continuous web using the combining roll.

In yet another embodiment, a diverter for laying an elastic member on a continuous web moving in a machine direction is provided. The diverter is a generally conical diverter having a groove. The groove has a pitch corresponding to an axial length of the groove as it wraps once around an outer surface of the diverter. The groove is configured for receiving the elastic member and for directing the elastic member out of an exit point of the groove. The diverter is configured for oscillating rotation, wherein rotation of the diverter moves the exit point in a cross machine direction.

While multiple embodiments are disclosed, still other embodiments of the invention will become apparent to those skilled in the art from the following detailed description, which shows and describes illustrative embodiments of the invention. As will be realized, the invention is capable of modifications in various obvious aspects, all without departing from the spirit and scope of the invention. Accordingly, the drawings and detailed description are to be regarded as illustrative in nature, and not as restrictive.

BRIEF DESCRIPTION OF THE DRAWINGS

While the specification concludes with claims particularly pointing out and distinctly claiming the subject matter which is regarded as forming the present invention, it is believed that the invention will be better understood from the following description, which is taken in conjunction with the accompanying drawings in which like designations are used to designate substantially identical elements, and in which:

DETAILED DESCRIPTION OF THE DRAWINGS

Figure 1:
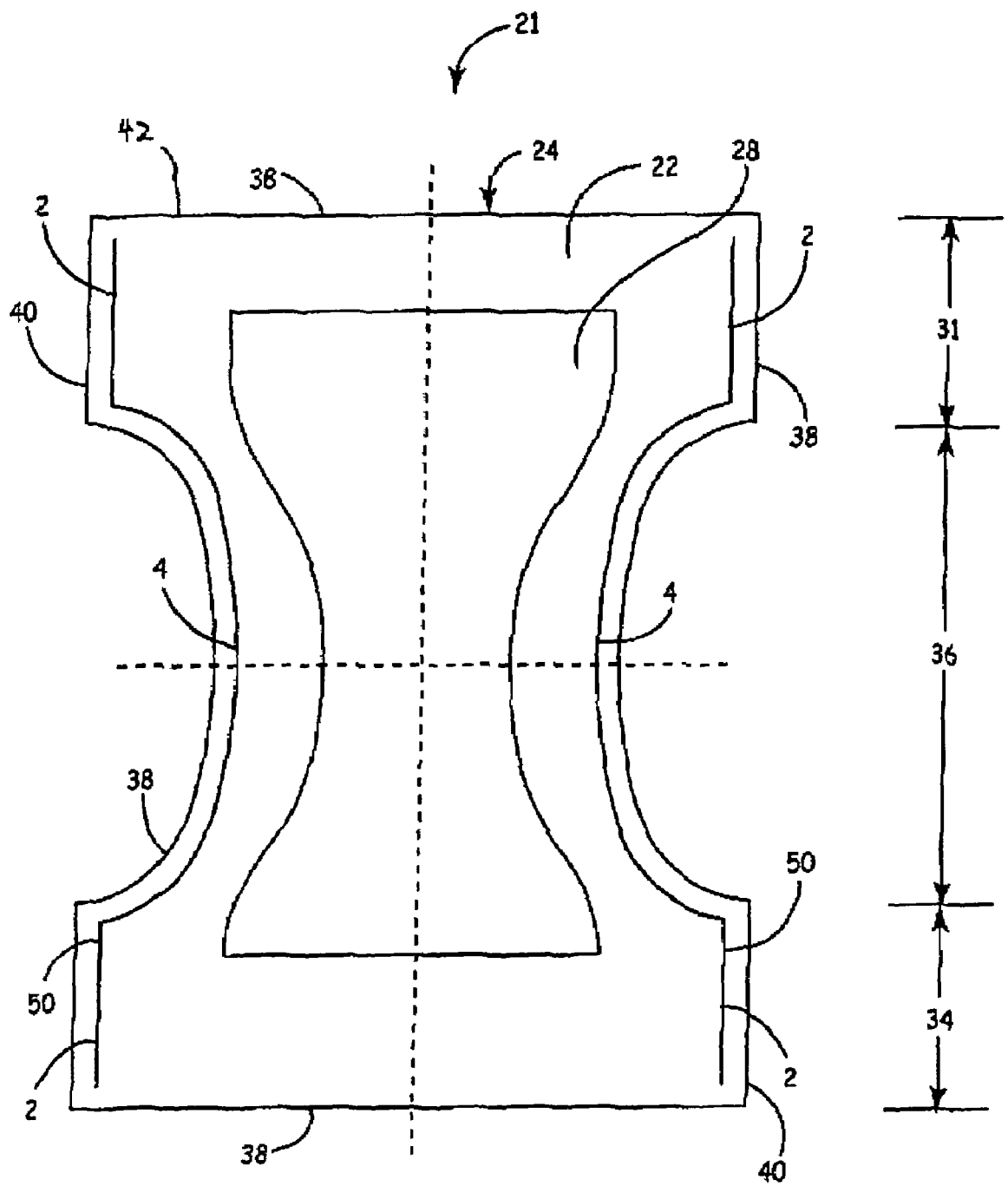
FIG. 1 illustrates a top view of an article manufactured according to the disclosed method in accordance with an embodiment.

A method for making absorbent articles such as diapers and training pants is provided. The method may be used for laying elastic members such as strands or ribbons in a nonlinear fashion on a continuous web. While nonlinear laying of the elastic member is focused upon, the method may alternatively be used to lay the elastic member in a linear fashion and/or in alternating linear and nonlinear fashions.

As used herein, the term "absorbent article" refers to devices that absorb and contain body exudates. Absorbent articles may be placed against or in proximity to the body of the wearer to absorb and contain the various exudates discharged from the body. Absorbent articles include devices designed to absorb urine, which are used by incontinent persons. Such incontinent articles include but are not limited to diapers, adult incontinent briefs, training pants, diaper holders, and liners. Other absorbent articles include those designed to absorb blood-based fluids such as menses. Such sanitary hygiene articles include tampons, catamenial pads, and the like. The term "disposable" is used herein to describe absorbent articles that are not intended to be laundered or otherwise restored or reused as an absorbent article (i.e., they are intended to be discarded after a single use and, preferably, to be recycled, composted or otherwise disposed of in an environmentally compatible manner).

As used herein, the term "absorbent core" refers to the portions (e.g., layers) of an absorbent article that function to acquire, distribute, transfer, store, and/or redistribute fluid. Acquisition materials include materials whose primary function is to acquire, and then relinquish, fluids. Such materials include acquisition layers, topsheet materials, transfer layers, flow control modules, wrap tissues, or nonwoven sheets designed to prevent migration of hydrogel forming polymers, etc.

As used herein, the term "front" refers to the portion of an article or absorbent core that is intended to be positioned proximate the front of a wearer. The term "rear" refers to the portion of an article or absorbent core that is intended to be positioned proximate the back of the wearer. As such, use of the relative term "in front of" means a position in the article or core more toward the front of the article or core, while the term "behind" means a position in the article or core more toward the rear of the article or core.

As used herein, the term "layers" refers to identifiable components of the absorbent structure, and any structure referred to as a "layer" may actually comprise a laminate or combination of several sheets or webs of the requisite type of materials as hereinafter described. As used herein, the term "layer" includes the terms "layers" and "layered." The term "upper" refers to the layer of the absorbent core that is nearest to and faces the article topsheet; conversely, the term "lower" refers to the layer of the absorbent core that is nearest to and faces the article backsheet. The various members, layers, and structures of absorbent articles may or may not be generally planar in nature, and may be shaped or profiled in any desired configuration.

As described below in detail, a method for manufacturing absorbent articles suitable for absorbing and retaining aqueous bodily liquids is provided. These absorbent articles generally include a backsheet including a substantially liquid impervious material, a topsheet, and an absorbent core disposed between the backsheet and the topsheet.

An embodiment of an absorbent article in the form of a diaper 21 that may be manufactured in accordance with the disclosed method is shown in FIG. 1. FIG. 1 is a top plan view of the diaper 21 in a flat-out, uncontracted state (i.e., with elastic-induced contraction removed) having a topsheet 22, a backsheet 24, and an absorbent core 28 positioned between the topsheet 22 and the backsheet 24. The backsheet 24 may, but is not required to, comprise an impermeable layer and a nonwoven web. One example of a suitable impermeable layer is a poly layer. The topsheet 22 is shown as being transparent so as to better illustrate the absorbent core 28. The layers of the diaper may be joined together at least about the periphery of the absorbent article.

Generally speaking, the diaper 21 includes a chassis having longitudinally opposed waist edges 42 and laterally opposed side edges 40. The laterally opposed side edges 40 are notched or curved to form leg openings. A crotch region 36 is provided generally between the longitudinally opposed waist edges and the laterally opposed side edges. Elastic members 50 may be provided along the laterally opposed side edges 40. As shown, the elastic members 50 are generally parallel to laterally opposed side edges 40, including in the notched or curved areas of the side edges. The layout of the elastic member on the article comprises the elastic profile. Specifically, the elastic profile may include, for example, linear portions 2 and curved portions 4. Using the disclosed method and apparatus, the length of the linear portions and curved portions and the number of linear portions and curved portions may be varied. Further, the degree of curvature, the angle of curvature, and the direction of curvature may be varied. Curved leg elastics may provide for a better fit to the wearer, less leakage, higher degree of comfort, and less red marking on the wearer.

Thus, as also shown in FIG. 1, the diaper 21 has a front waistband region 31, a back waistband region 34, a center region 36, and a periphery 38 having longitudinally opposed waist edges 42 and laterally opposed side edges 40. The side edges 40 are notched to form leg openings. The waistband regions 31 and 34 comprise the upper portions of the diaper 21 that, when worn, encircle the waist of the wearer. The center region 36 is that portion of the diaper 21 between waistband regions 31 and 34, and comprises that portion of the diaper 21 that, when worn, is positioned between the legs of the wearer and covers the lower torso of the wearer. Thus, the center region 36 defines the area of typical liquid deposition for a diaper 21 or other disposable absorbent article.

As previously noted, the diaper 21 may comprise elastic members that exert a contracting force on the diaper so that it configures more closely and more comfortably to the wearer. Elastic members can be assembled in a variety of well known configurations, such as those described generally in U.S. Pat. No. 3,860,003. Leg elastic members 50 may be disposed proximate to the periphery of the diaper, such as along each side edge 40 to form an elastically contractible leg cuff or side flap, so that the elastic members 50 tend to draw and hold the diaper against the legs of the wearer, all as shown in FIG. 1. The elastic members 50 may have a profile corresponding to the shape of the side edges of the article. As shown, the elastic members 50 include linear portions 2 and curved portions 4. The elastic profile thus comprises the linear portions 2 and the curved portions 4. The leg elastic members 50 may extend along a portion of the length of the diaper. Alternatively, the leg elastic members 50 may extend the entire length of the diaper, or any other length suitable to provide an elastically contractible line. The length of the leg elastic members 50 is guided by the diaper design. A barrier leg cuff including a barrier leg cuff elastic member may be disposed adjacent to each side edge 40 or between the side edge and a longitudinal centerline of the diaper 21.

Elastic members can be disposed adjacent either or both of the waist edges 42 of diaper 21 to provide a waistband as well as or rather than leg cuffs. See, for example, U.S. Pat. No. 4,515,595. The elastic members may be secured to the diaper 21 in an elastically contractible condition so that, in a normally unrestrained configuration, these elastic members effectively contract or gather the diaper 21. The elastic members can extend essentially the entire length of the diaper 21 in the center region 36, the entire length of the diaper 21, or any other length suitable to provide an elastically contractible line. The length of these elastic members is typically guided by the diaper's design. While the waistband can comprise a separate element affixed to the body of the disposable diaper, it alternatively may comprise an extension of other elements of the disposable diaper, such as the backsheet or the topsheet or both the backsheet and the topsheet. In one exemplary embodiment illustrated in the '595 patent, elastic waist elements extend across essentially the entire lateral width of the disposable diaper. Similar waistbands may be useful in designs wherein the elastic waist elements extend across only a portion of the lateral width of the diaper. In one embodiment, the elastic waist elements extend across a major portion of the lateral width of the disposable diaper.

The topsheet 22 is liquid pervious, so as to permit liquids (e.g., urine) to penetrate therethrough. Generally, the topsheet 22 may be compliant, soft feeling, and non-irritating to the wearer's skin. A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; thermoplastic scrims; other suitable materials; or combinations of these. Suitable woven and nonwoven materials can include natural fibers, e.g., wood or cotton fibers, synthetic fibers, e.g., polymeric fibers such as polyester, polypropylene, or polyethylene fibers, or a combination of natural and synthetic fibers. In one embodiment, the topsheet is made of a hydrophobic material to isolate the wearer's skin from liquids contained in the absorbent core that is treated on at least one side with a surfactant to allow liquids to readily penetrate therethrough. The topsheet 22 may comprise one or more layers.

High loft nonwoven topsheets and apertured formed film topsheets may be used. Apertured formed films are pervious to bodily liquids, non-absorbent, and have a reduced tendency to allow liquids to pass through in a direction away from the absorbent core and thereby rewet the wearer's skin. Thus, the surface of the formed film that is in contact with the body remains dry, thereby reducing bodily soiling and creating a more comfortable feel for the wearer. The body-facing surface of the formed film topsheet can be hydrophilic, thereby helping bodily liquids transfer through the topsheet faster and diminishing the likelihood that liquid will flow off the topsheet rather than flowing into and being absorbed by the absorbent core.

The backsheet 24 may be, but is not required to be, impervious to liquids (e.g., urine), and may permit vapors to escape from the absorbent core 28 (i.e., breathable). The backsheet 24 may prevent the exudates absorbed and contained in the absorbent core 28 from wetting articles that contact the diaper 21, such as bedsheets and undergarments. The backsheet 24 may comprise any suitable material, including a woven or nonwoven material, polymeric films such as thermoplastic films of polyethylene or polypropylene, composite materials such as a film-coated nonwoven material, other materials, or combinations of these. In the embodiments discussed, the backsheet 24 may comprise an impermeable layer and a breathable layer. The impermeable layer may comprise a poly material and the breathable layer may comprise a carrier nonwoven web. The impermeable layer may comprise a thermoplastic film having a thickness of from about 0.012 mm (0.5 mils) to about 0.051 mm (2.0 mils), although layers with a thickness outside this range may be used, and other flexible liquid impervious materials can be used. As used herein, the term "flexible" refers to materials that are compliant and that readily conform to the general shape and contour of the wearer's body. Suitable polymeric films for use as the impermeable layer may contain a high content of linear low density polyethylene. In some embodiments, the impermeable layer may include blends comprising about 45 to about 90% linear low density polyethylene and about 10 to about 55% polypropylene, or any other suitable quantities or ratios. Exemplary films for use as the impermeable layer are manufactured by Tredegar Industries, Inc. of Terre Haute, Ind. under the designations X-8323, RR8220 blend for certain blown films, and RR5475 blend for certain cast films, and are manufactured by Monsanto Chemical Corporation and marketed in the trade as Film No. 8020. The backsheet 24 may be embossed and/or matte finished to provide a more cloth-like appearance. In embodiments wherein the back portion comprises at least one absorbent core component, the backsheet may include a nonwoven web layer, an impermeable layer, and a cover layer. The at least one absorbent core component may be provided between the impermeable layer and the cover layer.

The absorbent core 28 is provided between the topsheet 22 and the backsheet 24. The absorbent core 28 may comprise any absorbent material capable of absorbing and retaining liquids such as urine and other body exudates. The absorbent core 28 may be provided in any suitable configuration, and it may comprise any suitable material or materials. For example, suitable materials include fibrous nonwoven materials, fibrous air-laid materials, fibrous wet-laid web materials, and combinations of fibrous materials having absorbent gelling materials dispersed upon or within the fibrous structure. The absorbent core may be formed into a packet having the fibrous materials substantially enveloped by a liquid pervious web that provides the structural integrity for the removal and replacement into the absorbent article. An exemplary form of a non-woven fibrous absorbent structure that may be utilized is constructed from hydrophilic chemically stiffened cellulosic fibers. Absorbent materials for use as the absorbent core may also be foam-based. For example, the absorbent core may include a foam material in the form of a sheet or a plurality of foam pieces or particles, which may be adhesively bonded together or which may simply be constrained into an unbonded aggregate held together by an overwrapping of envelope tissue or by means of the topsheet and backsheet of the absorbent article. The absorbent core can include a combination of materials, such as a combination of conventional elements or materials and one or more foam absorbent structures. For example, the absorbent articles may utilize an absorbent core that includes a combination, e.g., an airlaid mixture, of particles or pieces of the foam absorbent structures and conventional absorbent materials such as wood pulp or other cellulosic fibers and/or particles or fibers of polymeric gelling agents.

In manufacturing an absorbent article 21, a top portion and a back portion may be separately manufactured and then sealed together about at least portions of the peripheries thereof. Generally, the top portion includes the topsheet 22 and the back portion includes the backsheet 24. Other layers of the diaper may be allotted between the top portion and the back portion. Alternatively, the absorbent article 21 may be manufactured in a single process including laying the backsheet, laying layers of the diaper over the backsheet, laying the topsheet over the layers of the diaper, and laying elastic members on the diaper as desired. The layers of the diaper may include an absorbent core 28, an acquisition layer, a distribution layer, and/or others. The elastic members may be laid on any layer of the diaper. For the purposes of description, reference will be made to laying the elastic members on the backsheet of the diaper. Such reference is not intended to be limiting, as the elastics can be positioned in any desired manner.

Regardless of when associated, the topsheet 22 and the backsheet 24 may be associated along the peripheries thereof. Association may be in any suitable manner. As used herein, the term "associated" encompasses configurations where the topsheet is directly joined to the backsheet by affixing the topsheet directly to the backsheet, and configurations where the topsheet is indirectly joined to the backsheet by affixing the topsheet to one or more intermediate members that in turn are affixed to the backsheet. In one embodiment, the topsheet and the backsheet are affixed directly to each other by attachment means such as an adhesive or any other suitable attachment means. For example, a uniform continuous layer of adhesive, a patterned layer of adhesive, or an array of separate lines or spots of adhesive may be used to affix topsheet to the backsheet. Adhesives that have been found to be satisfactory are manufactured by Century Adhesives, Inc. of Columbus, Ohio and marketed as Century 5227; and by H. B. Fuller Company of St. Paul, Minn. and marketed as HL-1258. Generally, the layers may be joined in any suitable manner, including but not limited to adhesive, heat bonds, pressure bonds, ultrasonic bonds, dynamic mechanical bonds, any other suitable attachment, or combinations of these. See, e.g., U.S. Pat. Nos. 4,573,986 and 4,842,666, each herein incorporated by reference.

Figure 2:
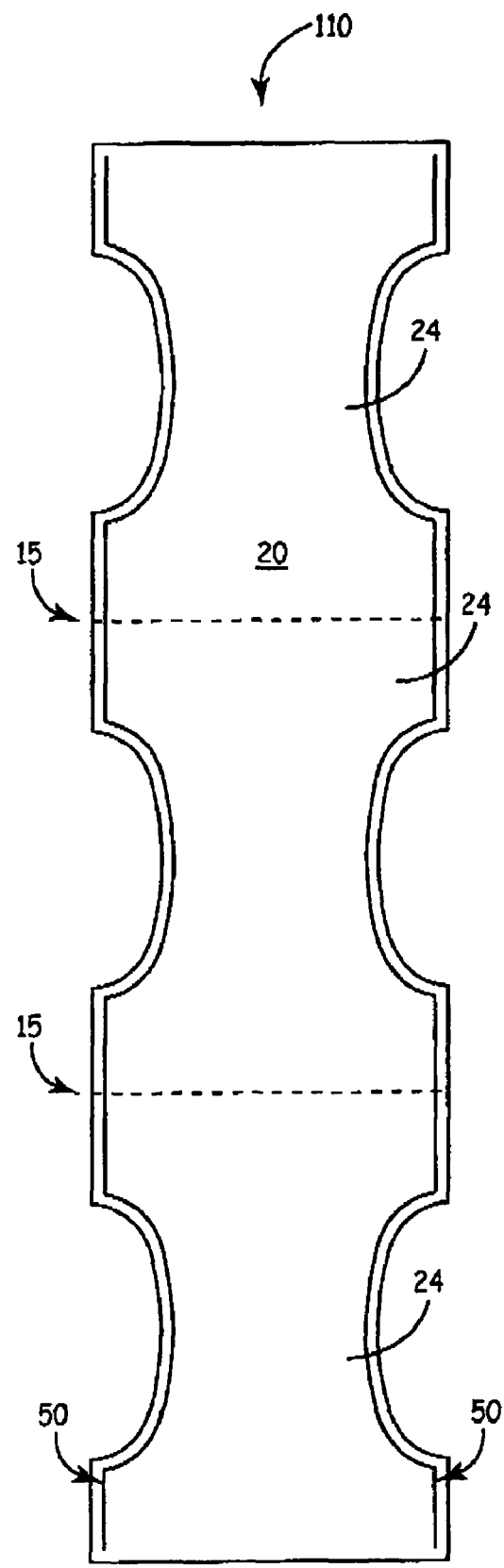
FIG. 2 illustrates a top view of a nonwoven web for forming articles in accordance with an embodiment.
Figure 3:
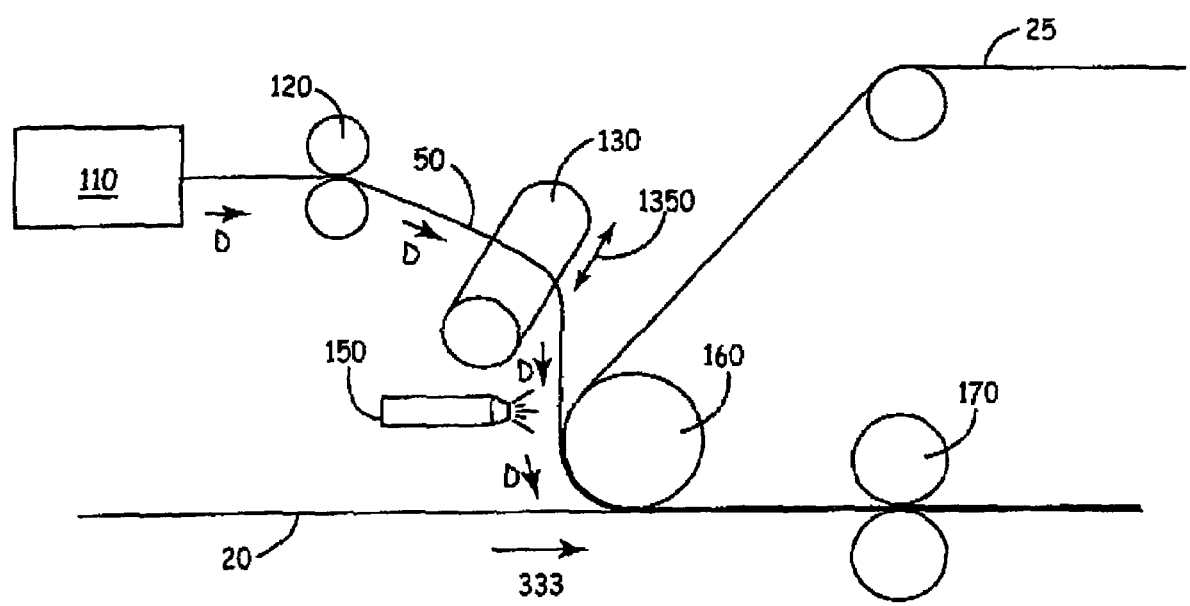
FIG. 3 illustrates a schematic system view of an apparatus setup for laying an elastic member in accordance with an embodiment.

As shown in FIGS. 2 and 3, an extensible nonwoven web 110 may be used to manufacture the backsheet. The nonwoven web 110 used for the backsheet 24 may be referred to as a carrier web. The carrier web 110 may be processed using a machine-direction process or a side-saddle process. In a machine direction process, a leading waist edge of an article undergoes each process before a trailing waist edge of the article. In a side saddle process, a leading side edge of an article undergoes each process before a trailing side edge of the article. The carrier web 110 comprising at least a portion of the backsheet 24 is conceptually divided along lines 15 to divide the carrier web 110 into article sections. In the embodiment of FIG. 2, the carrier web 110 is processed in the machine direction. As shown, using the disclosed method, elastic members 50 may be laid continuously along the carrier web. The elastic members 50 may form a portion of leg cuffs.

A method and apparatus for laying an elastic member in a nonlinear fashion on a continuous web is provided herein. As will be appreciated, the method and apparatus or portions thereof may be used to lay any component on a support. FIG. 3 illustrates an embodiment of an apparatus setup, including a diverter 130 and a combining roll 160, for laying the elastic member. As shown, a continuous web 20 is fed through an elastics station. The continuous web 20 is directed in the direction 333 beneath the combining roll 160. The elastic member 50 is directed in the direction D. A coupling mechanism 150, such as a glue gun or other suitable device, may also be provided for applying a coupling material to couple the elastic member 50 to the second web 25 and then to the continuous web 20. The coupling mechanism 150 may be provided proximate the elastic member 50 at any suitable location for applying a coupling material to the elastic member 50 before its association with the continuous web 20. As shown, the coupling mechanism 150 is provided generally proximate the combining roll 160. The elastic member 50 is fed to the elastics station. The elastic member 50 may comprise an elastic strand, an elastic ribbon, etc. In some embodiments, more than one elastic member may be fed to the elastics station. The elastic member 50 travels along the diverter 130 and is diverted in a cross machine direction 1350.

Figure 4A:
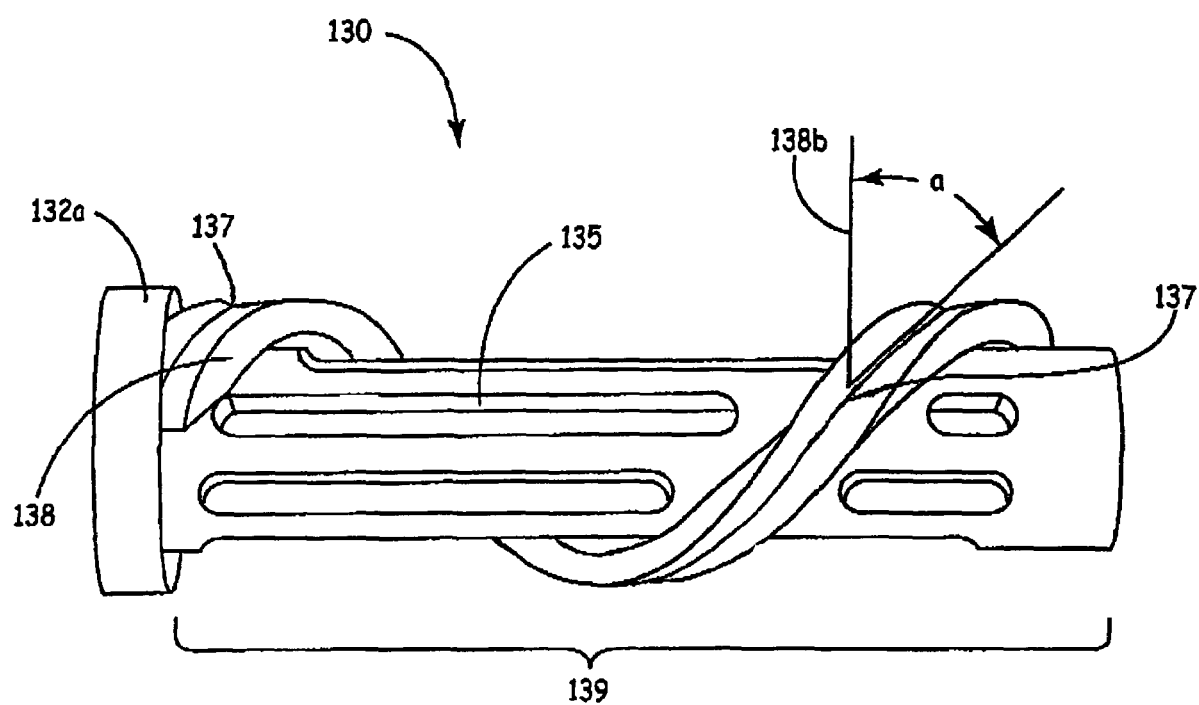
FIG. 4A illustrates a generally cylindrical diverter in accordance with an embodiment.

The elastic member 50 is directed around the combining roll 160 to a position over the continuous web 20. A second web 25 may also be fed around the combining roll 160 to a position proximate the elastic member 50. A supply 110 of elastic member 50 may be fed through an elastic metering system 120, which dispenses the material. Similarly, a metering station may be provided for the continuous web 20. The combining roll 160 may be chilled to advance settling of an adhesive used to couple the elastic member 50 to the continuous web 20. After the elastic member 50 has been laid on the continuous web 20, the web may be fed to a chill roll 170. The chill roll 170 adheres a second web 25 to the continuous web 20 proximate the elastic member 50. The elastic member 50 is thus captured between the continuous web 20 and the second web 25. The second web 25 may also set the adhesive (applied by coupling mechanism 150), hold the elastic profile, and return force if the elastic member has stretch. In one embodiment, the diverter 130 comprises a cylinder. The cylinder may be hollow, solid, partially hollow, it may have spokes, etc. In alternative embodiments, such as shown in FIGS. 25-29, the diverter 130 may be generally conical. Throughout this disclosure, embodiments of cylindrical diverters can be adapted for use in conical diverters, and vice versa, unless otherwise indicated. Any suitable configuration may be used. As seen in FIG. 4A, the diverter 130 comprises at least one groove 138 wrapping helically therearound. The groove 138 receives the elastic member 50 for laying the elastic member 50 on the continuous web 20. In order to lay more than one elastic member 50, more than one groove 138 may be provided on the diverter 130. For example, generally parallel grooves may be provided spaced apart from one another on the diverter 130 to lay generally parallel elastic members 50 on the continuous web 20.

Figure 4B:
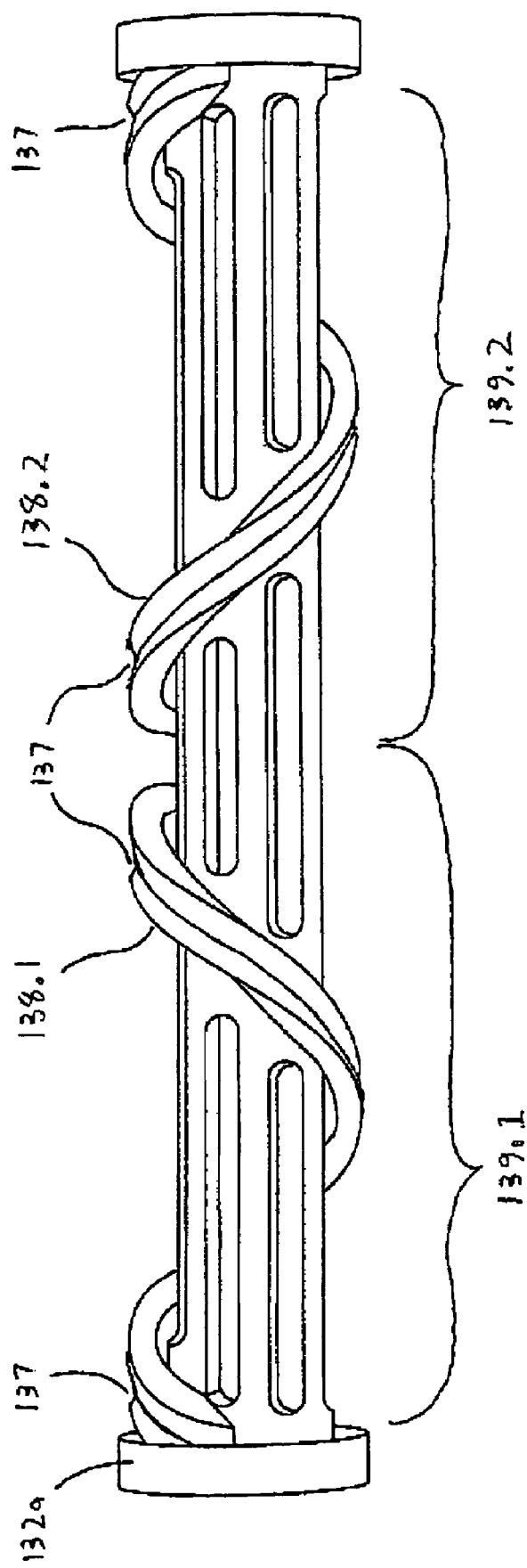
FIG. 4B illustrates a generally cylindrical diverter with two grooves in accordance with an embodiment.

In an alternative embodiment, shown in FIG. 4B, two grooves 138.1, 138.2 may be provided on the diverter in opposite directions to lay elastic members 50 on opposite sides of the continuous web 20. For such embodiment, the pitch of the grooves may be longer or the diverter 130 may be wider. FIG. 4B illustrates an embodiment wherein the diverter 130 is approximately twice as long as the diverter 130 shown in FIG. 4A. As shown, a first groove 138.1 is shown extending in one direction and a second groove 138.2 is shown extending in the opposite direction. Thus, the diverter 130 of FIG. 4B can be used to lay elastic members 50 on opposite sides of the continuous web.

The groove 138 may be formed in any suitable manner. In one embodiment, the groove 138 can be included on a raised section on the diverter 130. In another embodiment, the groove 138 is cut into the surface of the diverter 130. In another embodiment, the groove 138 may comprise a cut on a raised section of the diverter 130. The groove 138 has a pitch. The pitch 139 (139.1 and 139.2 in FIG. 4B) is the axial length of the groove 138 as it wraps once around the outer circumference of the diverter. The pitch 139 can be determined and referenced via its angle $\alpha$ relative to a line 138b drawn generally perpendicular to the axis of rotation of the diverter 130. As discussed more fully below, the pitch 139 of the groove 138 contributes to the setup of the elastics station. The pitch 139 may be set at any suitable length. In one embodiment, the pitch is about 7.5 inches. In another embodiment, the pitch is about 4.25 inches. In the embodiment shown, the groove 138 makes one complete revolution around the diverter 130. In other embodiments, the groove 138 may make less than or more than one complete revolution around the diverter 130.

The groove 138 includes a receiving portion 137 for receiving the elastic member 50. As shown, the receiving portion 137 is formed by an open surface on the outer side relative to the axis of rotation of the diverter 130. The elastic member 50, as received by the groove 138, conforms to the bottom of the groove 138. The diverter 130 may be manufactured of a sufficiently light weight material to permit rapid servo motor response and duty cycle. In the embodiment shown, openings 135 are provided in the diverter 130 to reduce inertia of the diverter 130. Mounting of the diverter 130 to a motor, such as a servo motor, may be done in any suitable manner. For example, a hole may be machined in a face plate 132a of the diverter 130 generally concentric to the rotational axis of the diverter 130. Further, a second motor may be provided on the end opposite to the first motor. Alternatively, a bearing supporting the weight of the diverter 130 may be provided at the end opposite to the first motor.

During rotation of the diverter 130, the diverter 130 oscillates back and forth, thus moving the groove 138 back and forth. The groove 138 in turn moves the exit point of the elastic member 50 from the diverter 130, thus moving the travel path of the elastic member from the diverter 130 to the combining roll 160 in the cross-machine direction. The exit point of the elastic member 50 from the diverter 130 can be any point along the groove 138 and the point will determine where on the continuous web 20 the elastic at that point is laid. Thus, the exit point from the groove 138 varies according to the elastic profile being laid. Generally, the exit point will be the point of the groove perpendicular to the combining roll 160 at any given time. The oscillation of the diverter 130 may be controlled by a software program controlling a motor running the diverter 130. The direction of rotation and speed of rotation, including not rotating the diverter, may be set to affect the elastic profile. Thus, the elastic profile laid on the continuous web 20 via the combining roll 160 is easily customized. Further, to repeat the elastic profile or to cause the elastic member to have repeated curvatures, the diverter 130 may complete more than one revolution.

Figure 5A:
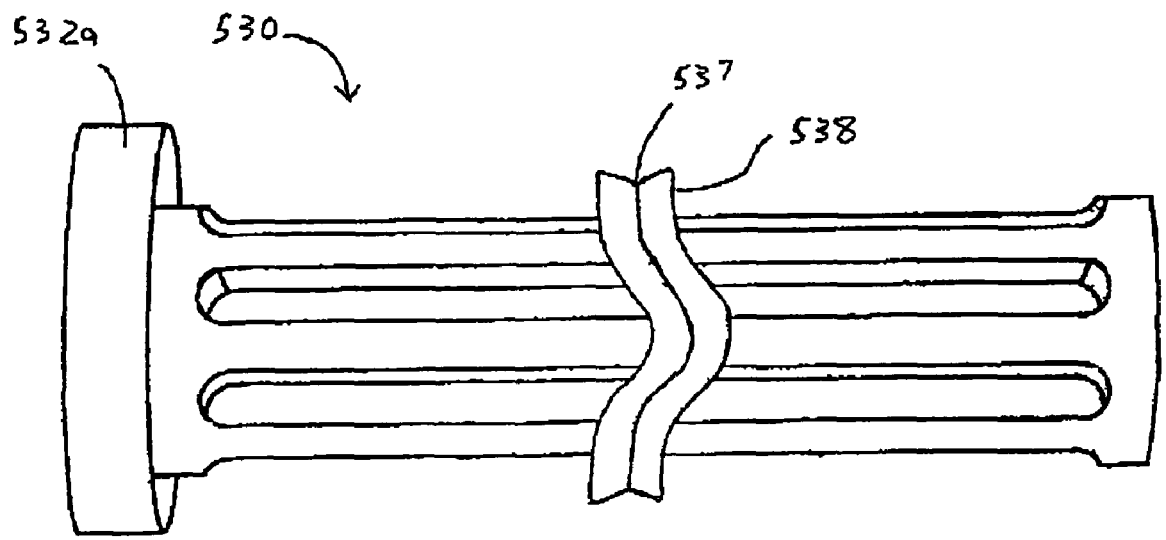
FIG. 5A illustrates a generally cylindrical diverter with a continuous groove in accordance with an embodiment.

FIG. 5A illustrates a generally cylindrical diverter 530 with a continuous groove 538 in accordance with an embodiment. The cylindrical diverter 530 includes a face plate 132a and the continuous groove 538. The groove 538 includes a receiving portion 537 for receiving the elastic member 50. The continuous groove 538 wraps continuously around a circumference of the diverter 530. The continuous groove 538 can move an exit point of an elastic member from the diverter 530, thus moving the travel path of the elastic member from the diverter 530 to a combining roll in the cross-machine direction, as described in herein. Since the continuous groove 538 is continuous, the cylindrical diverter 530 can continuously rotate in a single direction while allowing an elastic strand to remain in the continuous groove 538. In some embodiments, the cylindrical diverter 530 can rotate with varying speeds or can even come to a stop, to change the rate at which the elastic member moves in the cross-machine direction, which can, in turn, change a placement of the elastic member, as will be understood by one of ordinary skill in the art.

Figure 5B:
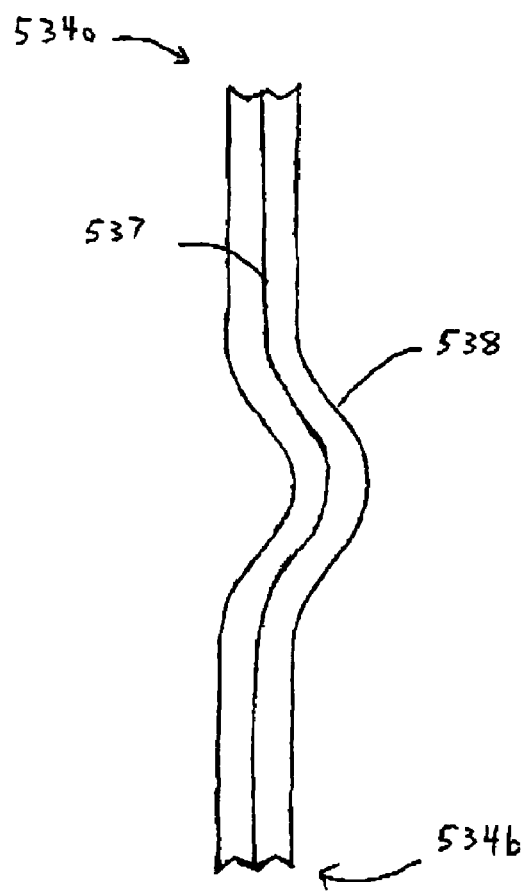
FIG. 5B illustrates a top view of the continuous groove of FIG. 5A, laid out flat, in accordance with an embodiment.

FIG. 5B illustrates a top view of the continuous groove 538 of FIG. 5A, laid out flat, in accordance with an embodiment. The groove 138 includes the receiving portion 537. In the embodiment of FIG. 5B, the groove 538 includes a first end 534a and a second end 534b, which are illustrated as broken. When the continuous groove 538 wraps continuously around the circumference of the diverter 530, as illustrated in the embodiments of FIG. 5A, the first end 534a and the second end 534b are aligned and connected together to form the continuity of the continuous groove 538, as will be understood by one of ordinary skill in the art.

Figure 6:
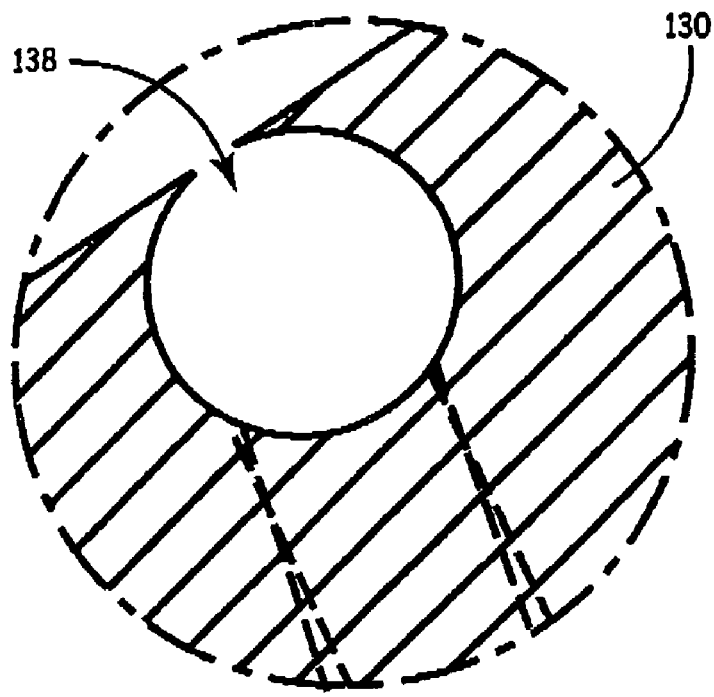
FIG. 6 illustrates a cross-sectional view of a generally round groove of a diverter in accordance with an embodiment.
Figure 7:
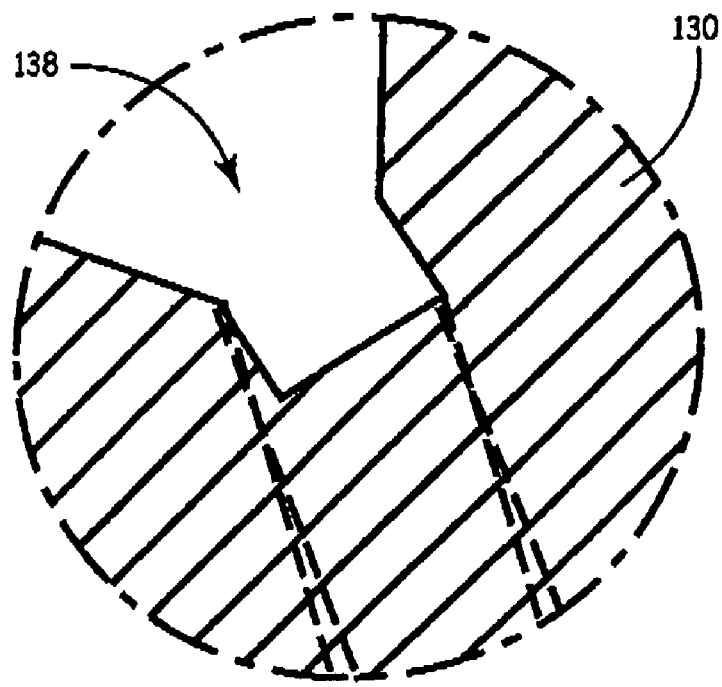
FIG. 7 illustrates a cross-sectional view of a groove of a diverter having a partially rectilinear and partially trapezoidal cross section in accordance with an embodiment.
Figure 8:
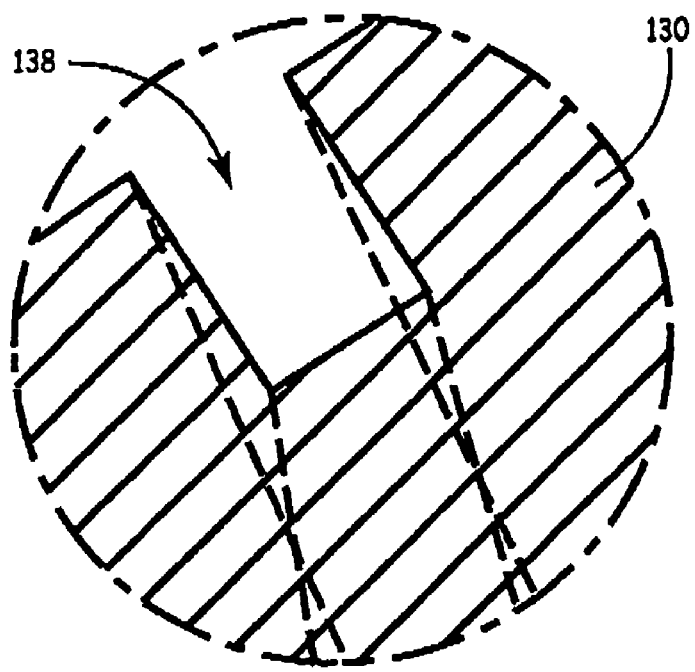
FIG. 8 illustrates a cross-sectional view of a generally rectilinear groove of a diverter in accordance with an embodiment.
Figure 9:
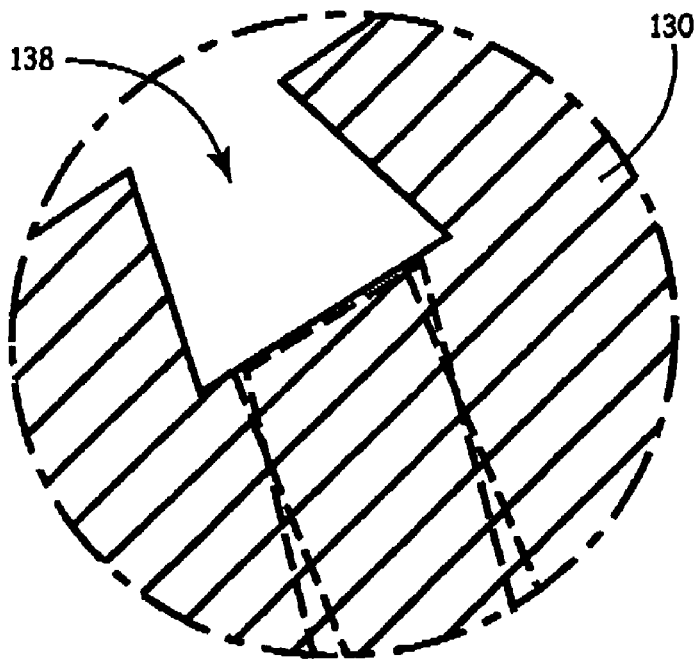
FIG. 9 illustrates a cross-sectional view of a generally trapezoidal groove of a diverter in accordance with an embodiment.

FIGS. 6-10 illustrate suitable cross sectional shapes of the groove 138 of the diverter 130. Such cross-sectional shapes may be used with any shape of diverter 130. In one embodiment, the groove 138 is machined into the material of the diverter 130. For example, the diverter 130 may comprise aluminum and the aluminum may be machined to exhibit the groove 138. A low friction wear resistant coating may be applied to the groove 138 to facilitate movement of the elastic member in the groove. In one embodiment, the groove may have a width of about 0.063 inch and a depth of about 0.250 inch for processing a round strand of elastic material having a diameter of about 0.010 inch. Variation to the groove dimensions may be as narrow as the material passing therethrough to a width approximately 40 times the width of the material. The depth may range, for example, from approximately 0.001 inch to approximately 2 inches, or any other desired depth. As illustrated in FIGS. 6-10, the cross-sectional shape of the groove 138 may be varied as appropriate for a given application. The groove may be substantially rectilinear, as shown in FIG. 8, trapezoidal, as shown in FIG. 9, round, as shown in FIG. 6, a combination, as shown in FIG. 7, or any other desired configuration.

Figure 10:
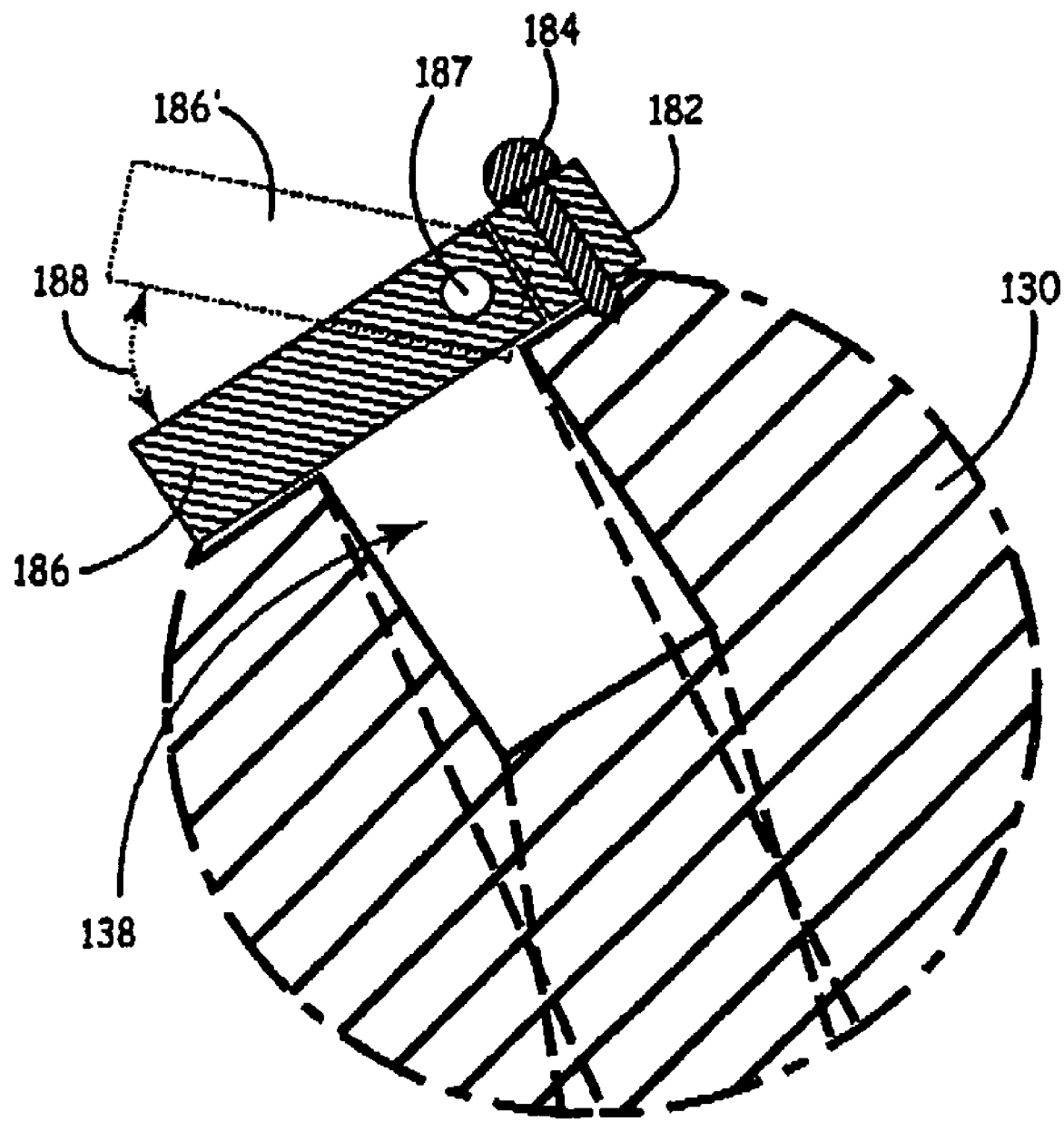
FIG. 10 illustrates a cross-sectional view of a groove of a diverter having a closure device in accordance with an embodiment.

As shown in FIG. 10, a closure device 186 may be provided with the diverter 130 to close at least a portion of the groove 138. The closure device 186 may aid to retain the elastic in the groove 138. The closure device 186 may include a hinge 187 for hinged rotation to permit opening of the closure device 186 for easy threading of the elastic member into the groove 138. The closure device 186 is positioned against the diverter 130 to close the groove 138. The closure device 186 may be pivoted 188 to position 186' to gain access to the groove 138. In some embodiments, during pivoting 188 of the closure device 186, a portion 182 of the closure device may be stationary. This portion 182 may include a coupling mechanism to couple the closure device 186 to the groove 138. The closure device 186 may be coupled to the diverter 130 in any suitable manner. For example, the closure device 186 may be coupled to the diverter 130 using a screw 184. A closure device 186 may be used with any cross sectional shape of the groove 138.

Figure 11:
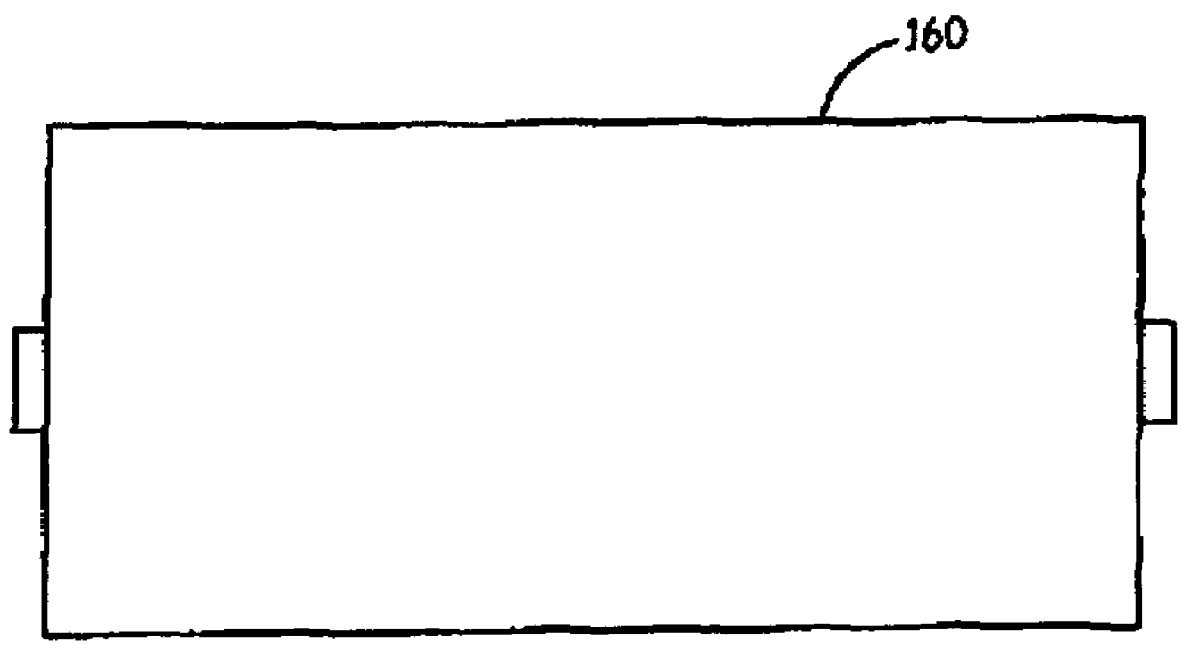
FIG. 11 illustrates a combining roll in accordance with an embodiment.

FIG. 11 illustrates a combining roll 160. The combining roll 160 is provided over the continuous web 20 (see, for example, FIG. 3) and functions to direct and press the elastic member 50 to the continuous web 20. The combining roll 160 is generally cylindrical and may have a width at least as wide as the portion of the continuous web 20 over which the elastic member 50 is to be laid. The combining roll 160 may be driven by a servo motor. Face plates may be provided on one or both ends of the combining roll for fixing to a support or for fixing to the servo motor.

Figure 12:
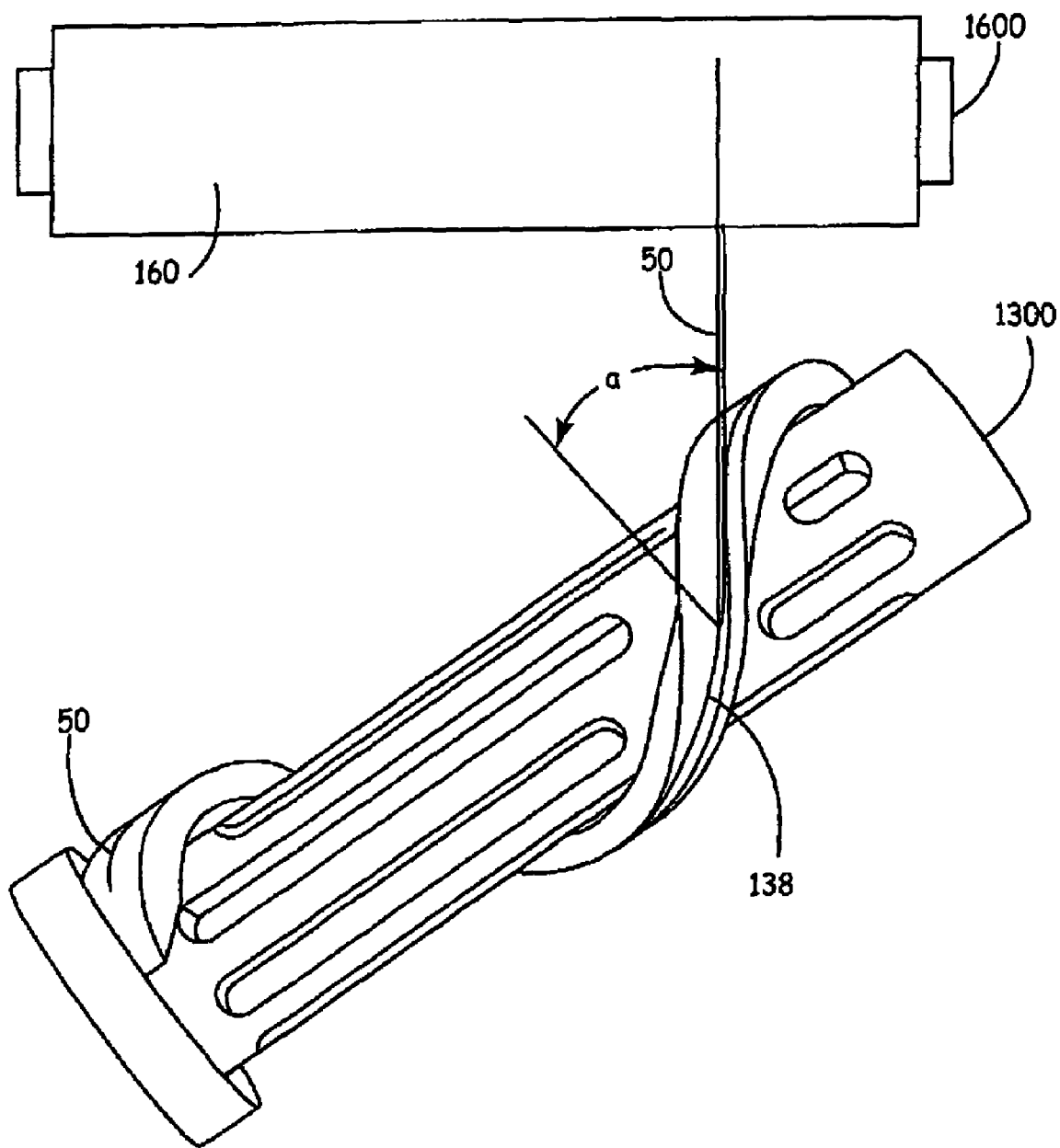
FIG. 12 illustrates a top view showing the relative orientation of a generally cylindrical diverter and a combining roll in accordance with an embodiment.

FIGS. 12-18 illustrate a configuration of the diverter 130 and the combining roll 160 to form the elastics station. The relative positioning of the diverter 130 and the combining roll 160 affects the elastic profile resulting from the transfer of the elastic member 50 to the continuous web 20 from the point that the elastic member 50 exits the diverter 130. The direction of travel of the elastic member 50 is shown by direction D. As shown in FIG. 12, the angle α of the groove 138 sets the angle of the axis of rotation 1300 of the diverter 130 relative to the axis of rotation 1600 of the combining roll 160. More specifically, the positioning is selected such that an elastic member 50 exiting the groove 138 travels to the combining roll 160 at an orientation substantially perpendicular to the axis of rotation of the combining roll 160. The elastic member 50 thus has a generally perpendicular approach to the combining roll 160. This approach reduces bending of the elastic member 50 as the elastic member 50 exits the diverter 130.

The steeper the angle α between the diverter 130 and the combining roll 160 (the angle being determined by the pitch of the groove 138), the faster the elastic member 50 moves back and forth across the combining roll 160 as the diverter 130 is rotated.

Figure 13:
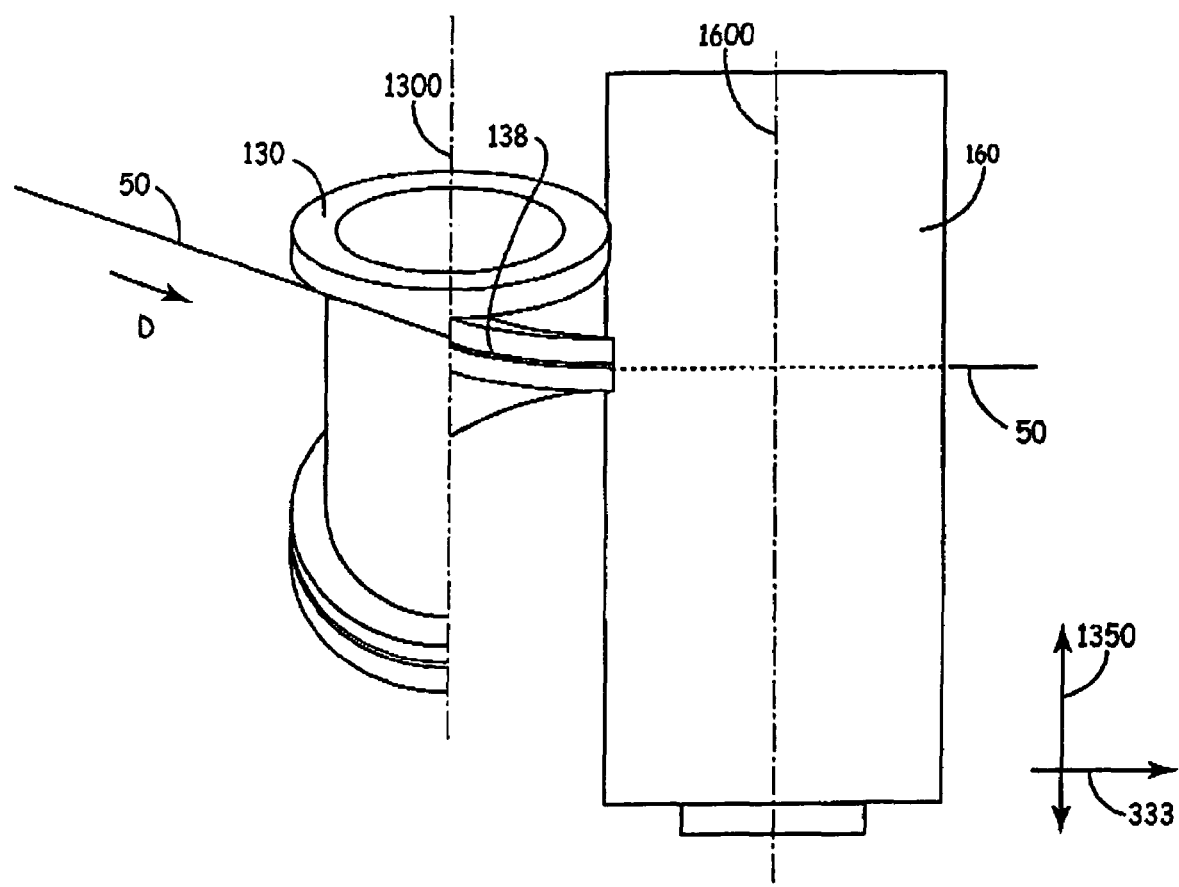
FIG. 13 illustrates a top view showing the relative orientation of a generally cylindrical diverter and a combining roll wherein the axis of rotation of the generally cylindrical diverter and the axis of rotation of the combining roll are generally parallel in accordance with an embodiment.

In another embodiment, as shown in FIG. 13, the axis of rotation 1300 of the diverter 130 and the axis of rotation 1600 of the combining roll 160 may be generally parallel. When the axis of rotation 1300 of the diverter 130 and the axis of rotation 1600 of the combining roll 160 are generally parallel, a smooth travel path for the elastic member 50 to exit from the groove 138 of the diverter 130 and travel to the combining roll 160 is achieved. This setup further provides a consistent cross machine travel path through the adhesive application is achieved. The machine direction, or direction of travel of the continuous web, is referenced by numeral 333 while the cross machine direction is referenced by numeral 1350. As discussed with reference to FIGS. 27-28, the outer surfaces of the diverter 130 and the combining roll 160 may be generally parallel while the axes of rotation thereof are not by providing a generally conical diverter 133.

Figure 14:
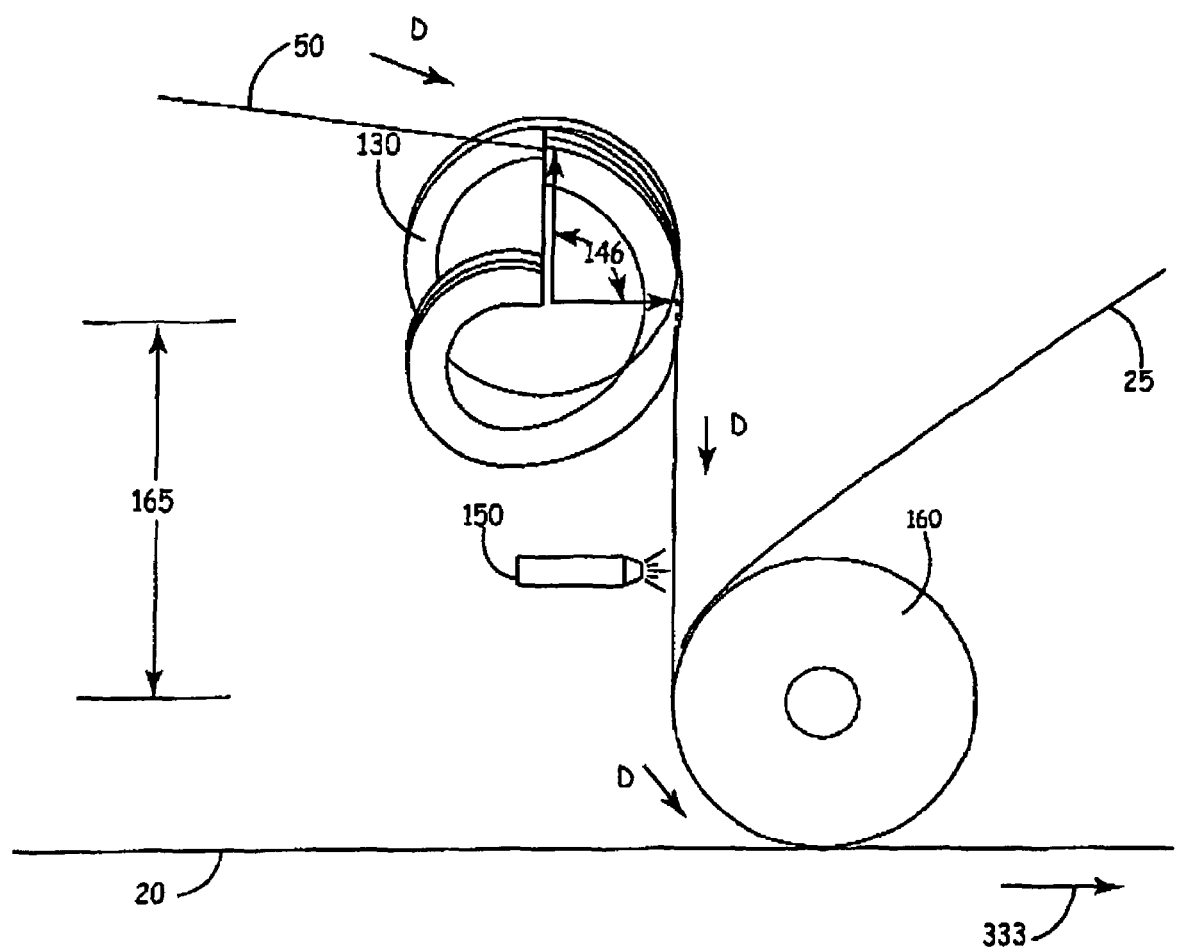
FIG. 14 illustrates a schematic view of an elastics station including a generally cylindrical diverter and a combining roll in accordance with an embodiment.

The diverter 130 and the combining roll 160 are set apart at a height 165, shown in FIG. 14. The height 165 represents the distance between where the elastic member 50 exits the diverter 130 and where the elastic member 50 contacts the combining roll 160. The speed at which the elastic member 50 travels in the cross machine direction is related to the distance represented by the height 165. When the diverter 130 rotates, the elastic member 50 is pulled along the angle 1316 (see FIG. 15) between the diverter 130 and the combining roll 160. The elastic member 50 automatically travels in a generally vertical path exiting the diverter 130 to the combining roll 160. Thus, the path the elastic member 50 travels initially is angled as the diverter 130 rotates. The angle of the elastic member 50 to the diverter 130 as the elastic member 50 exits the diverter may be referred to as the elastic path angle. This angle automatically transitions to be perpendicular with the diverter 130 such that the elastic path becomes tangent to the diverter 130 as the elastic member 50 automatically travels in the generally vertical path exiting the diverter 130 to the combining roll 160. A longer distance of the height 165 creates a shallower elastic path angle, resulting in slower cross machine travel speed. Correspondingly, a shorter distance of the height 165 creates a steeper elastic path angle, resulting in faster cross machine travel speed. Any suitable height 165 may be used, for example ranging from approximately 10 mm to approximately 300 mm, or in other examples heights outside this range. In one embodiment, the height 165 is approximately 70 mm. The degree of elastic wrap around the diverter 130 may be referred to as the wrap angle 146. In one embodiment, the method utilizes an approximately 90 degree wrap angle 146. This angle may be reduced down to approximately 10 degrees (or another suitable angle) or increased to multiple revolutions around the diverter 130. FIG. 14 further illustrates the continuous web 20 traveling in the machine direction 333. As shown, a coupling mechanism 150 may be provided for applying a coupling material to couple the elastic member 50 to the second web 25 and then to the continuous web 20.

Figure 15:
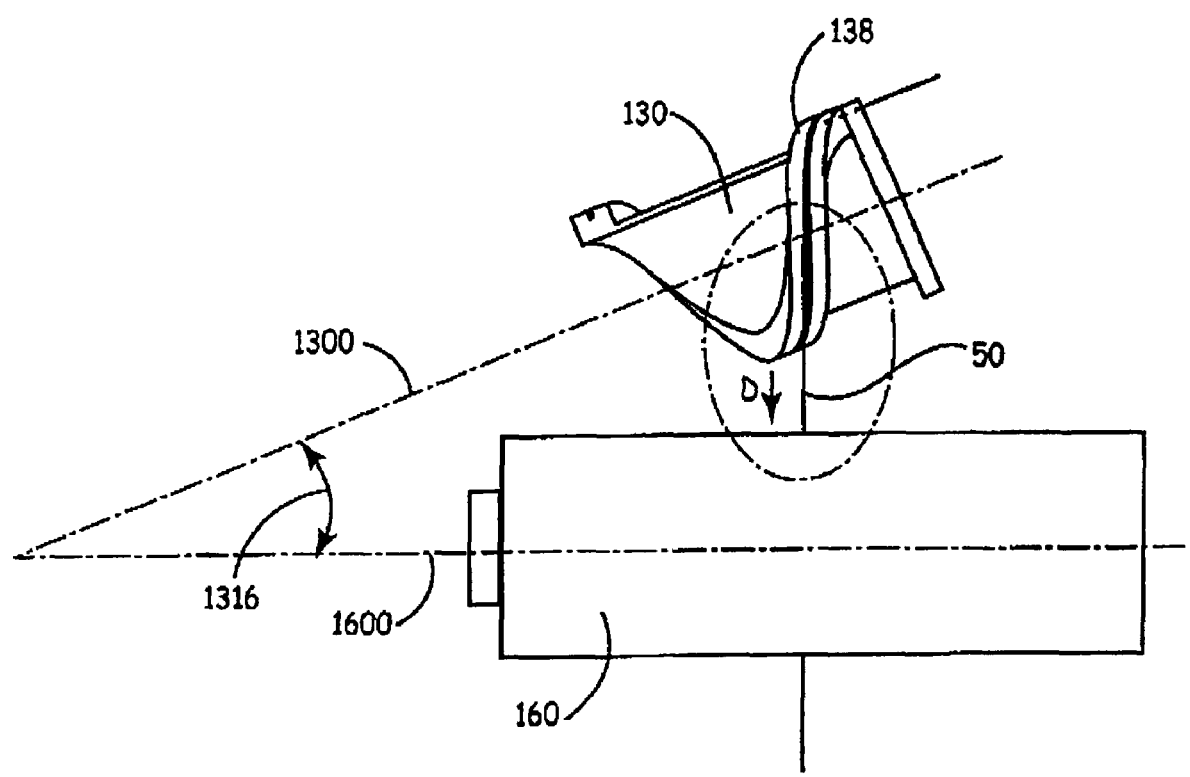
FIG. 15 illustrates a top view showing the angle between the axis of rotation of the generally cylindrical diverter and the axis of rotation of the combining roll in accordance with an embodiment.

In the embodiment of FIG. 15, the diverter 130 and the combining roll 160 have generally nonparallel axes 1300, 1600. The angle 1316 of the axis of rotation 1300 of the diverter 130 relative to the axis of rotation 1600 of the combining roll 160 is set to create a generally perpendicular angle between the combining roll axis 1600 and the exit point of the groove 138 of the diverter 130. Arranging the diverter 130 and the combining roll 160 at such an angle offers a smooth open channel for the elastic member 50 to exit. The angle 1316 of the axis of rotation 1600 of the combining roll 160 with respect to the axis of rotation 1300 of the diverter 130 is thus related to the pitch of the groove 138. The pitch of the groove 138 can be determined by the cross machine movement the elastic member 50 travels for one rotation of the diverter 130. Because, in this embodiment, the diverter 130 is set at an angle to create a generally perpendicular exit opening of the groove to the combining roll 160, some of the cross machine movement may be lost. For example, in an embodiment where the diverter 130 has a pitch of about 4.25 inch, the groove may be on about a 36 degree angle relative to the mounting surface of the diverter drive motor, in which case the diverter 130 is set on about a 36 degree angle relative to the combining roll 160 to create the generally perpendicular angle to the combining roll 160. Diverters 130 having longer pitches generally require the set-up angle to be steeper to create the generally perpendicular portion of the groove 138 where the elastics exit to the combining roll 160. This steeper angle reduces the amount of actual cross machine movement compared to the pitch of the groove 138 on the diverter 130. Clockwise and counter clockwise rotation oscillations of the diverter 130 divert the elastic in the cross machine direction.

The rotation of the diverter 130 and the oscillation of the rotation of the diverter 130 generally sets the elastic profile. Oscillation of rotation of the diverter 130 in the clockwise and counterclockwise directions move the exit point of the elastic member 50 from the groove 138 on the diverter 130. The degree of rotation and the speed of rotation impact the elastic profile. Further, the speed of the continuous web 20 can impact the elastic profile. More specifically, the speed of the continuous web 20 can affect the speed at which it pulls the elastic member 50 away from the diverter 130. Thus, a slower carrier web speed generally will result in a steeper travel path of the elastic member 50. As previously discussed, as the diverter 130 rotates, an elastic path angle is created between the contact point of the elastic member 50 with the combining roll 160 and the exit point of the elastic member 50 from the groove 138 of the diverter 130. This elastic path angle automatically transitions such that the elastic member 50 is drawn tangent to the diverter 130, thus moving the contact point of the elastic member 50 with the combining roll 160, thereby moving the elastic profile. Thus, movement of the elastic profile starts when the diverter 130 is rotated a degree of rotation. This moves the exit point on the diverter 130 and the elastic profile curves until the elastic path is tangent to the diverter 130. Thus, faster rotation movement and a larger degree of rotation will result in steeper profiles and farther movements or greater curvatures.

In one embodiment, the diverter 130 has a pitch of about 4.25 inch. To create cross machine movement less than about 4.25 inches, the diverter 130 may be set to rotate less than one rotation. For example, the diverter 130 may be set to rotate about 90 degrees to generate about 1.063 inches of cross machine movement of the elastic minus the amount lost resulting from the set-up angle. In alternative embodiments, the diverter 130 may have a pitch of between approximately 1 inch and 25 inches, or any other suitable pitch whether or not outside this range, for moving material less or more with one or more rotations of the diverter 130.

Figure 16:
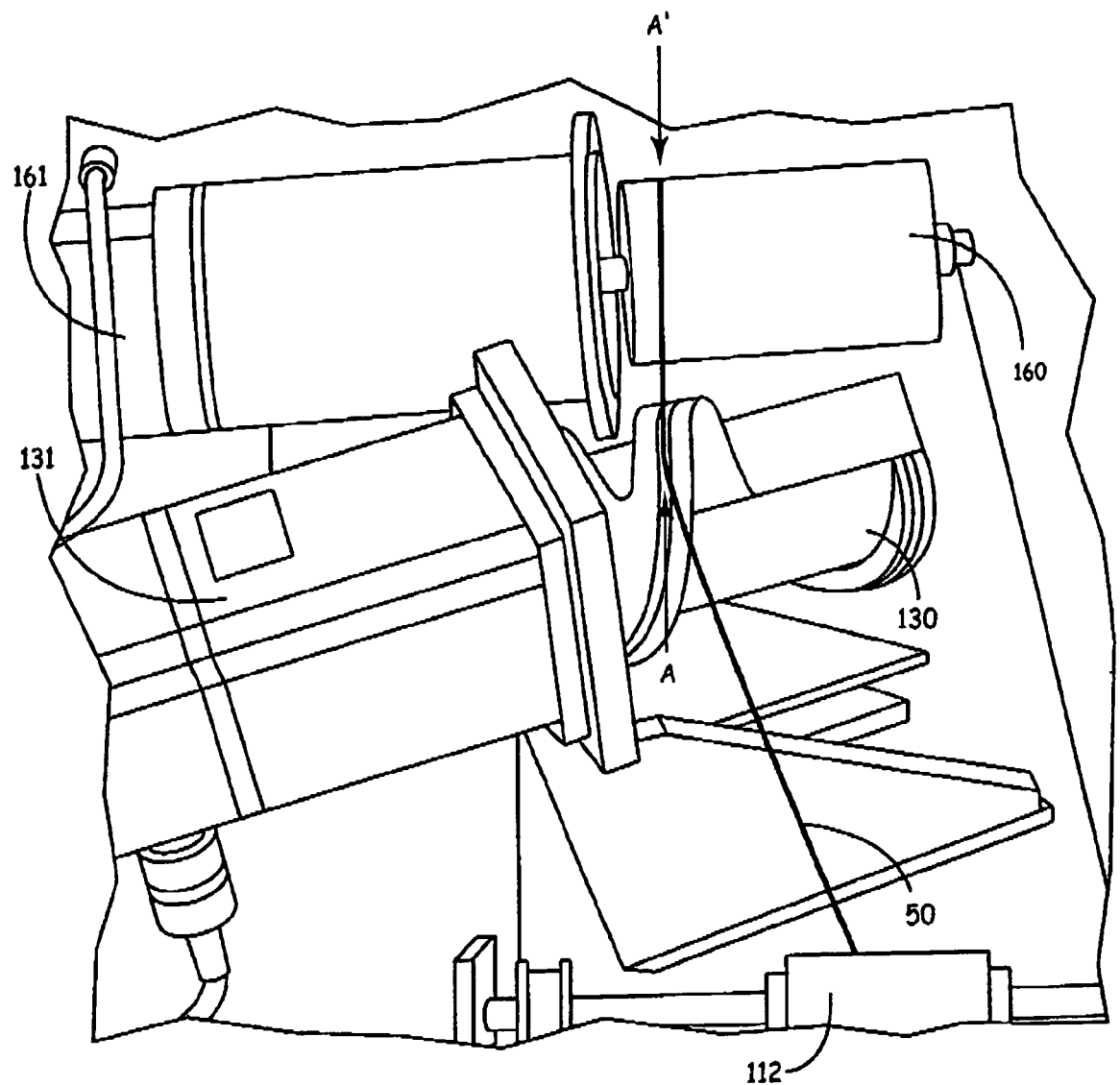
FIG. 16 illustrates a perspective view of a diverter, elastic member, and combining roll with the diverter at a first rotational position in accordance with an embodiment.
Figure 17:
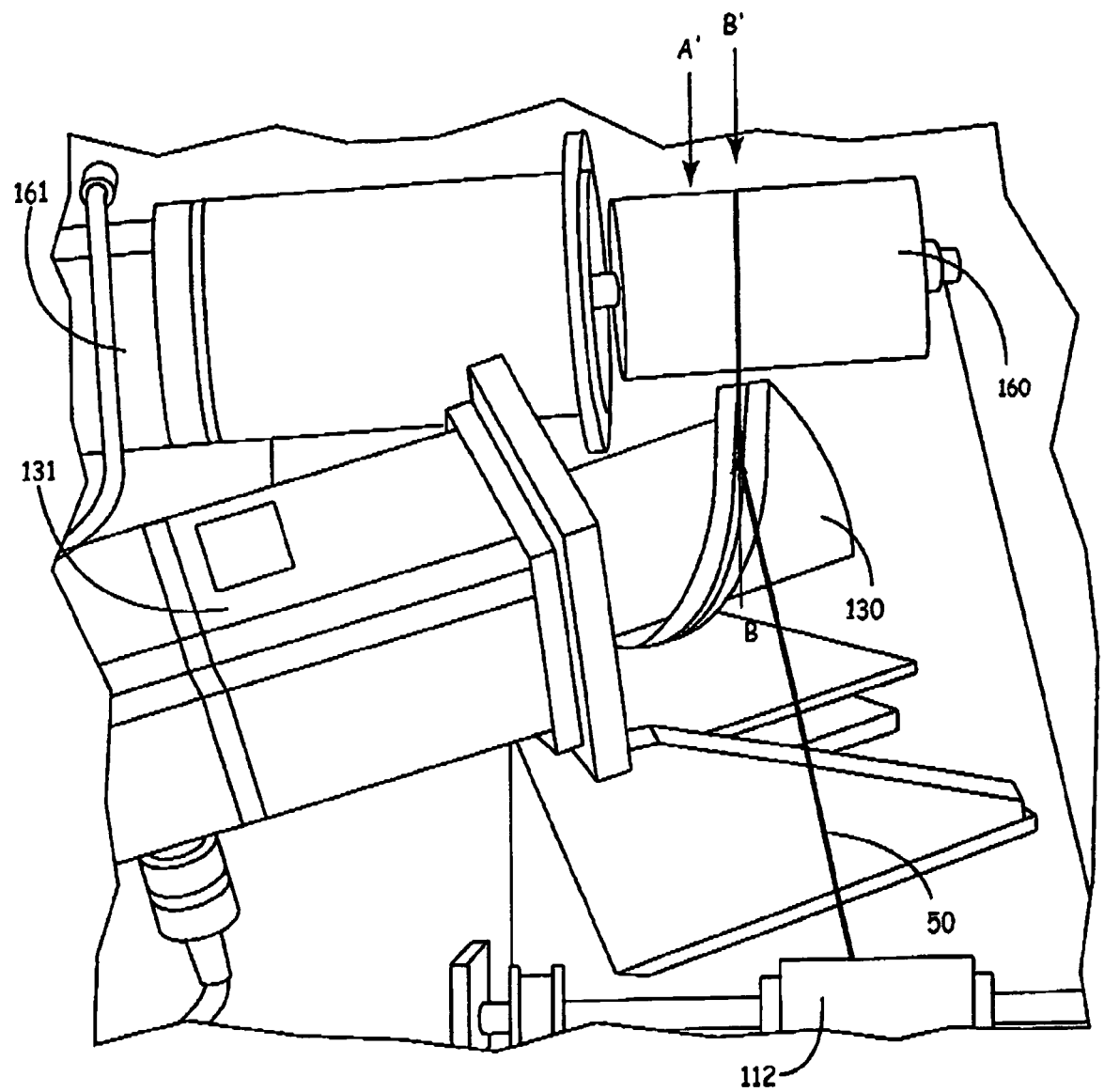
FIG. 17 illustrates a perspective view of a diverter, elastic member, and combining roll with the diverter at a second rotational position in accordance with an embodiment.
Figure 18:
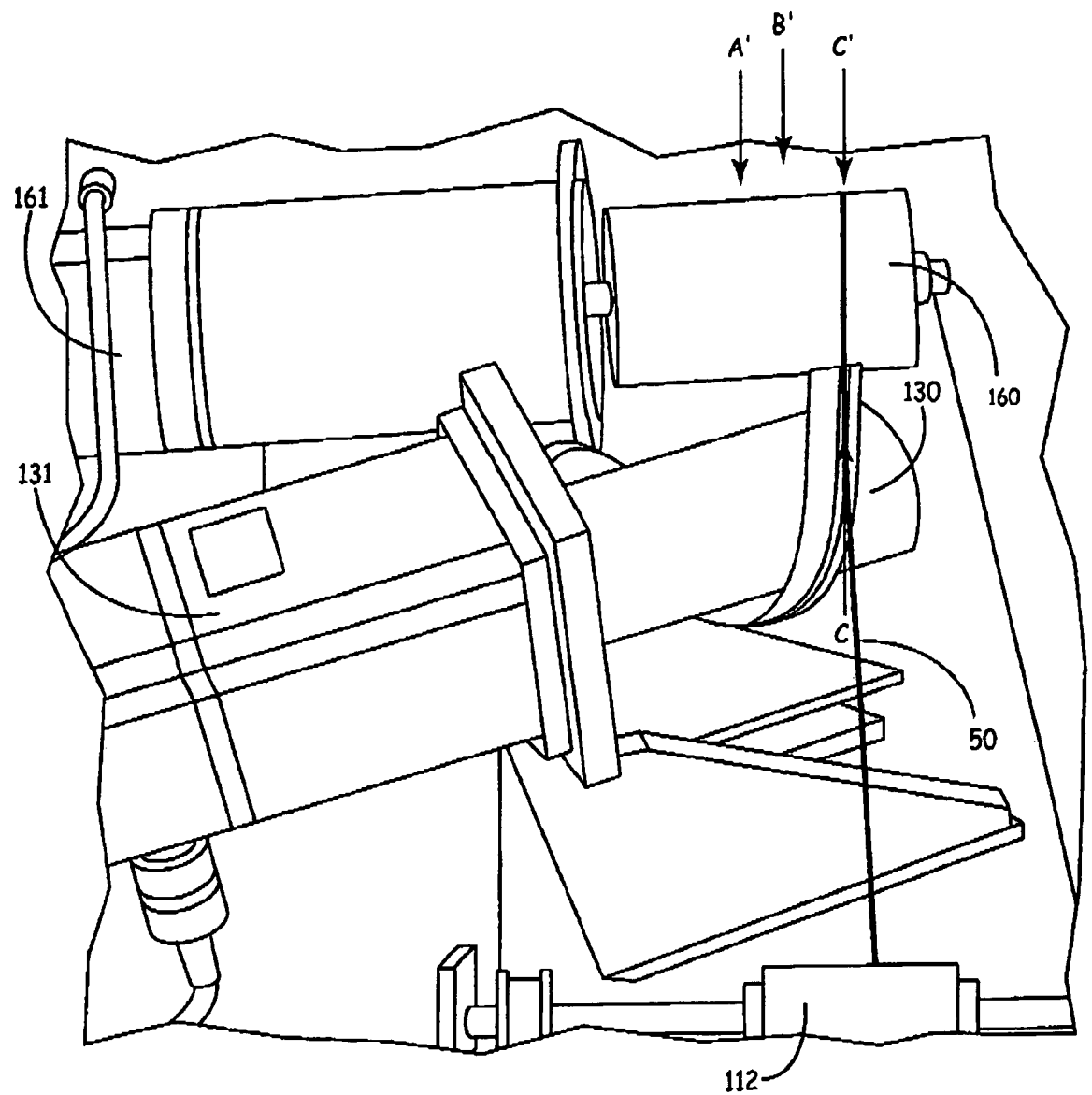
FIG. 18 illustrates a perspective view of a diverter, elastic member, and combining roll with the diverter at a third rotational position in accordance with an embodiment.

FIGS. 16-18 illustrate the diverter 130 at different rotational positions (A, B, and C) and the corresponding cross machine direction position (A', B', C') of the elastic member 50 on the combining roll 160. As shown, motors 131, 161, such as servo motors, may be provided for driving the diverter 130 and combining roll 160 respectively. The elastic profile is related to the exiting point of the elastic member 50 from the diverter 130. For example, the diverter 130 may be positioned at a particular cross machine location where the elastic member 50 makes a tangent path to the combining roll 160. The diverter 130 may then be rotated clockwise and stopped to locate an exiting point in a different cross machine location. The elastic member 50 then follows in the direction of the new exiting point. The diverter 130 may then be rotated counter clockwise to reposition the exiting point to the original location, again moving the path of the elastic member.

As shown, a guide roller 112 is provided upstream of the diverter 130 to hold the elastic member 50 in a fixed cross machine direction location. The combining roll 160 is positioned downstream of the diverter 130. In FIG. 16, the elastic member 50 exits the diverter 130 at position A and is applied to the combining roll 160 at a left position, position A'. In FIG. 17, the elastic member 50 exits the diverter 130 at a position B is applied to the combining roll 160 at a central position, position B'. In FIG. 18, the elastic member 50 exits the diverter 130 at a position C is applied to the combining roll 160 at a right position, position C'. The position of the elastic member 50 on the combining roll 160 is set by the position of the exiting point of the elastic member 50 from the diverter 130. Thus, in FIG. 16, the diverter 130 is located in its farthest most counter clockwise position, position A, creating an angle that the elastic member 50 will follow downstream—approximately tangent from the exit point of the groove 138 to the combining roll 160. FIG. 17 illustrates about 180 degrees of clockwise rotation of the diverter 130 with respect to the rotation position of the diverter in the embodiment of FIG. 16. FIG. 18 illustrates an additional about 180 degrees of clockwise rotation of the diverter 130 with respect to the rotation position of the diverter in the embodiment of FIG. 17.

The exit point of the elastic member 50 from the groove 138 and, thus, the elastic profile, is set by setting the rotational movement of the diverter 130. The rotational movement of the diverter 130 sets the exit points of the elastic member 50 from the groove 138 and thus the position of the elastic member 50 on the combining roll 160. This setting can be done by changing the software driving the diverter 130, for example, by changing or adjusting software for a servo motor 131.

Figure 19:
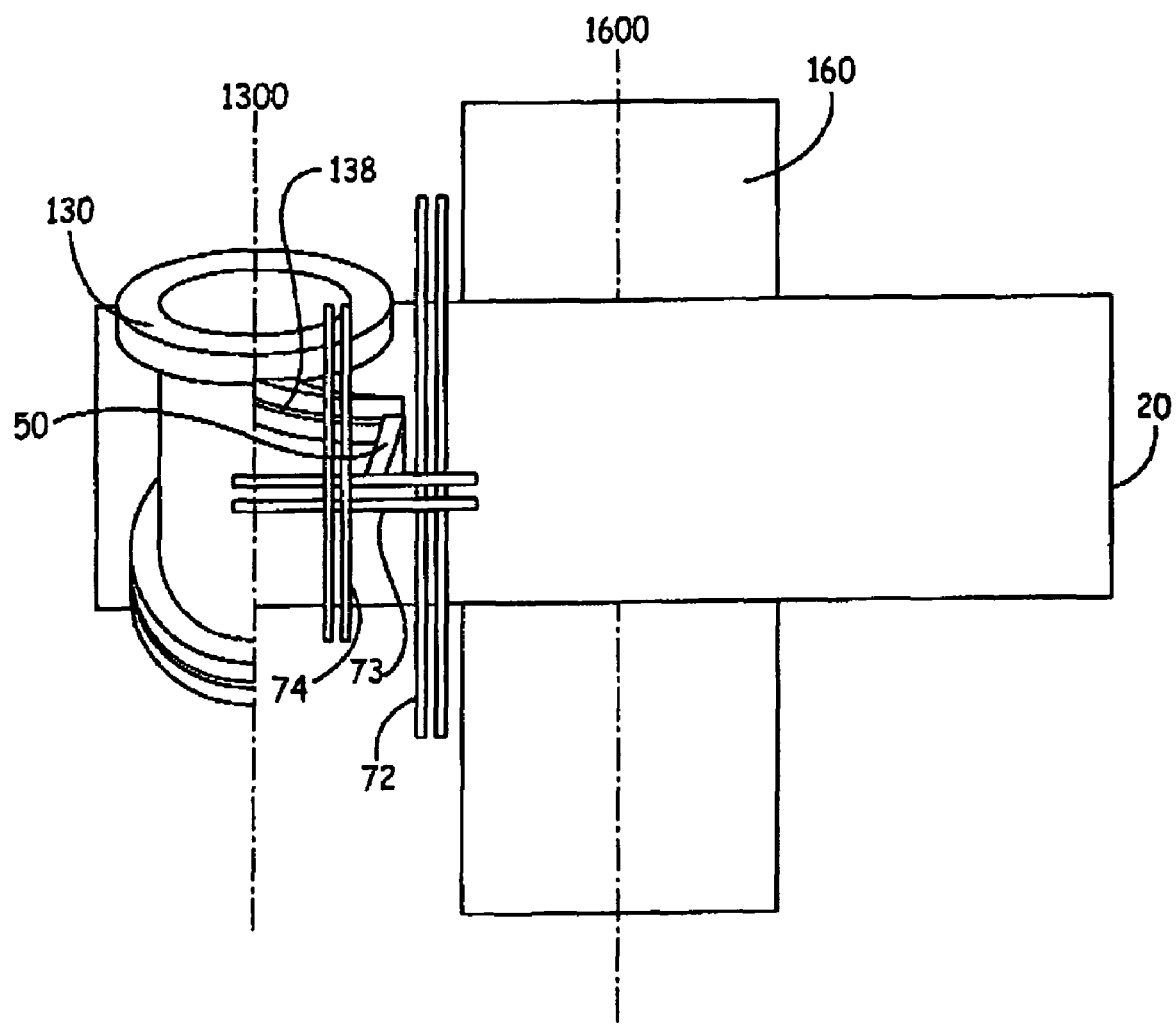
FIG. 19 illustrates a top view of an elastics station including a generally cylindrical diverter and a combining roll in accordance with an embodiment, the elastics station being configured for laying an elastic ribbon.
Figure 20:
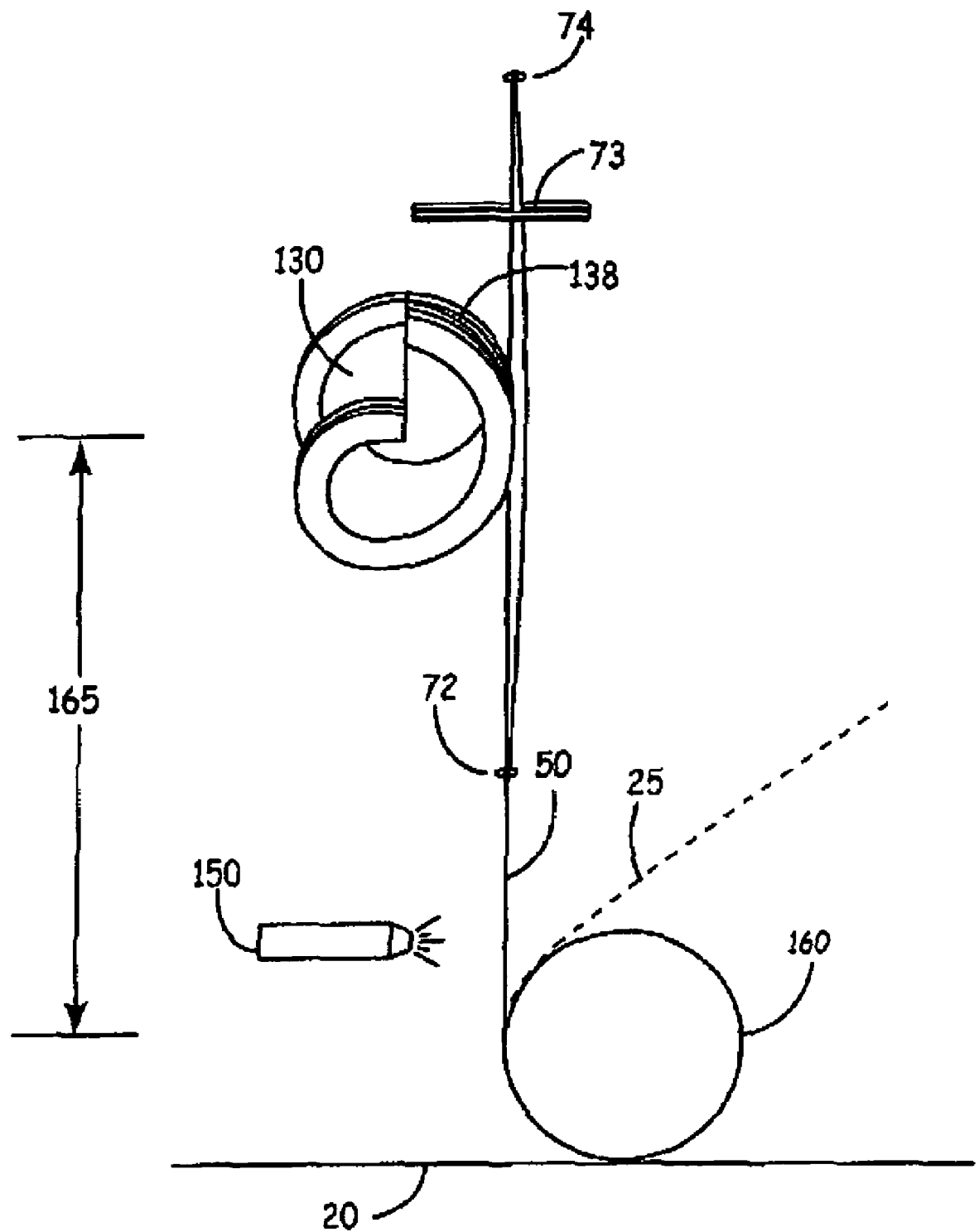
FIG. 20 illustrates a schematic view of an alternative view of the elastics station of FIG. 19.
Figure 21:
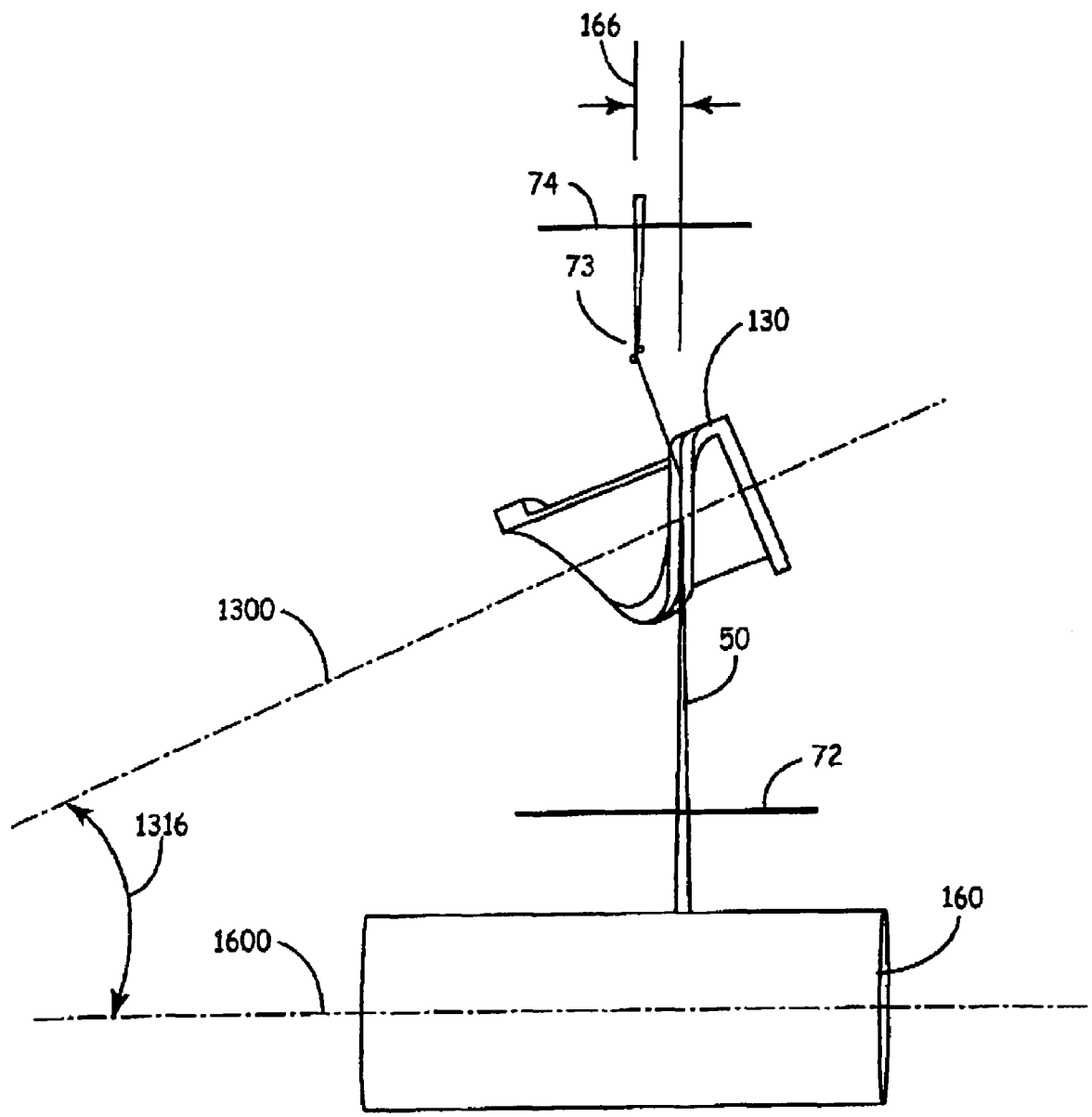
FIG. 21 illustrates a top view showing the angle between the axis of rotation of the generally cylindrical diverter and the axis of rotation of the combining roll of the elastics station of FIG. 19 in accordance with an embodiment.

FIGS. 19-21 illustrate an alternate embodiment suited for laying an elastic ribbon in a nonlinear fashion. The embodiments of FIGS. 19-21 generally represent variations of the embodiments of FIGS. 13-15, which show an embodiment generally suited for laying an elastic strand. As shown in FIG. 18, the elastics station comprises a diverter 130 having an axis of rotation 1300, a combining roll 160 having an axis of rotation 1600, a first positioning member 74, a second positioning member 73, and a third positioning member 72 (see also FIG. 20). A groove 138 is provided on the diverter 130 for receiving the elastic member 50. The depth of the groove 138 may be any suitable dimension, or as shallow as possible while still maintaining the elastic member 50 in place within the groove 138. The first positioning member 74 holds the elastic member 50 in the orientation that is metered to the elastic station. The second positioning member 73 positions the elastic member 50 in the orientation maintained by the groove 138 and to isolate cross machine movement of the elastic member 50 upstream of the diverter 130. In an alternative embodiment for isolating cross machine movement, the second positioning member 73 may be moved to maintain the elastic member 50 in line with the groove 138 as the diverter rotates. Such movement of the second positioning member 73 may add additional control to maintain the elastic member 50 in position in the groove 138 at rapid isolating rates. The third positioning member 72 positions the elastic member 50 at an orientation for receipt by the combining roll 160. Thus, a smooth transition is provided between the groove 138 of the diverter 130 and placement of the elastic member 50 on the continuous web 20 on the combining roll 160. The positioning members may comprise one or more rollers, rotating turning bars, idlers, or other. Generally, a rotating bar refers to a bar that turns or twists the elastic member 50 while an idler refers to a bar or support that supports the elastic member 50 without turning or twisting the elastic member 50. Thus, the positioning members may be dynamic, or may be generally static. The positioning members may have a rotation such that the elastic member 50 travels along the rotation of the positioning members or may have no rotation. In one embodiment, the first positioning member 74 and the third positioning member 72 each comprise a set of rotating turning bars and the second positioning member 73 comprises a set of idlers.

In the embodiment of FIG. 20, the elastic member 50, for example a ribbon, travels directly through the groove 138 and does not wrap the diverter 130 (see FIG. 24) as an elastic strand might. Thus, the elastic ribbon does not have a wrap angle. If permitted to wrap around the diverter 130, the ribbon may wrinkle and/or deform. As previously discussed, first, second, and third positioning members 74, 73, and 72, respectively may be provided to reduce wrinkling or deformation of the ribbon. As shown, the diverter 130 and the combining roll 160 are set apart at a height 165. The height 165 represents the distance between where the elastic member exits the diverter 130 and where the elastic member contacts the combining roll 160. The speed at which the elastic member 50 travels in the cross machine direction is related to the distance represented by the height 165. When the diverter 130 rotates, the elastic member 50 is pulled along at an angle 1316 (see FIG. 21) between the diverter 130 and the combining roll 160. The angle 1316 is the angle of the axis of rotation 1300 of the diverter 130 to the axis of rotation 1600 of the combining roll 160. The elastic automatically travels in a vertical path exiting the diverter 130 to the combining roll 160. Thus, the path the elastic member 50 travels initially is angled as the diverter 130 rotates. The angle of the elastic member 50 to the diverter 130 as the elastic member 50 exits the diverter may be referred to as the elastic path angle. This angle automatically transitions to be perpendicular with the diverter 130 such that the elastic path becomes tangent to the diverter 130 as the elastic member 50 automatically travels in the generally vertical path exiting the diverter 130 to the combining roll 160. A longer distance of the height 165 creates a shallower elastic path angle, resulting in slower cross machine travel speed. Correspondingly, a shorter distance of the height 165 creates a steeper elastic path angle, resulting in faster cross machine travel speed. Any suitable height 165 may be used, for example ranging from approximately 10 mm to approximately 300 mm, or figures outside this range. In one embodiment, the height 165 is approximately 70 mm. An adhesive applicator 150 is provided to apply adhesive to the elastic member 50 and a second web 25 for placement proximate the elastic member 50 to secure the elastic member 50 to the second web 25 and then to the continuous web 20.

In the embodiment of FIG. 21, the diverter 130 and combining roll 160 have generally nonparallel axes 1300, 1600. The angle of the axis of rotation 1300 of the diverter 130 relative to the axis of rotation 1600 of the combining roll 160 is set to create a generally perpendicular angle between the combining roll axis 1600 and the groove 138 of the diverter 130 at the point where the elastic member 50 exits the groove 138. Arranging the diverter 130 and the combining roll 160 at this angle offers a smooth open channel for the elastic member 50 to exit. The angle 1316 of the axis of rotation 1600 of the combining roll 160 relative the axis of rotation 1300 of the diverter 130 is thus related to the pitch of the groove 138. The pitch of the groove 138 is a function of the cross machine movement the elastic member 50 travels for one rotation of the diverter 130. Because, in this embodiment, the diverter 130 is set at an angle to create a generally perpendicular exit opening of the groove to the combining roll 160, some of the cross machine movement may be lost. FIG. 21 further illustrates the first positioning member 74, the second positioning member 73, and the third positioning member 72. As shown, the first positioning member 74 is provided upstream of the diverter 130 and for maintaining the elastic member 50 in an orientation as provided in the groove 138 and to isolate cross machine movement of the elastic member 50 upstream of the diverter 130. The second positioning member 73 is provided between the rotating rollers 74 and the diverter 130. The second positioning member 73 orients the elastic member 50 for receipt by the groove 138 of the diverter 130. The third positioning member 72 is provided between the diverter 130 and the rotating roll 160. The third positioning member 72 orients the elastic member in a configuration for receipt by the combining roll 160. Maintaining correct orientation of the elastic member 50 aids in preventing the elastic ribbon from flipping or becoming twisted, which may impact the quality of the finished article.

FIG. 21 illustrates an embodiment wherein a second positioning member 73, puts the elastic ribbon 50 in the same orientation as the groove 138. A first positioning member 74 maintains the elastic ribbon 50 in the orientation received by the elastics station for direction to the second positioning member. In alternative embodiments, a single positioning member may be provided in place of the first and second positioning members 74, 73 wherein the single positioning member puts the elastic ribbon 50 in the same orientation as the groove 138.

Figure 22:
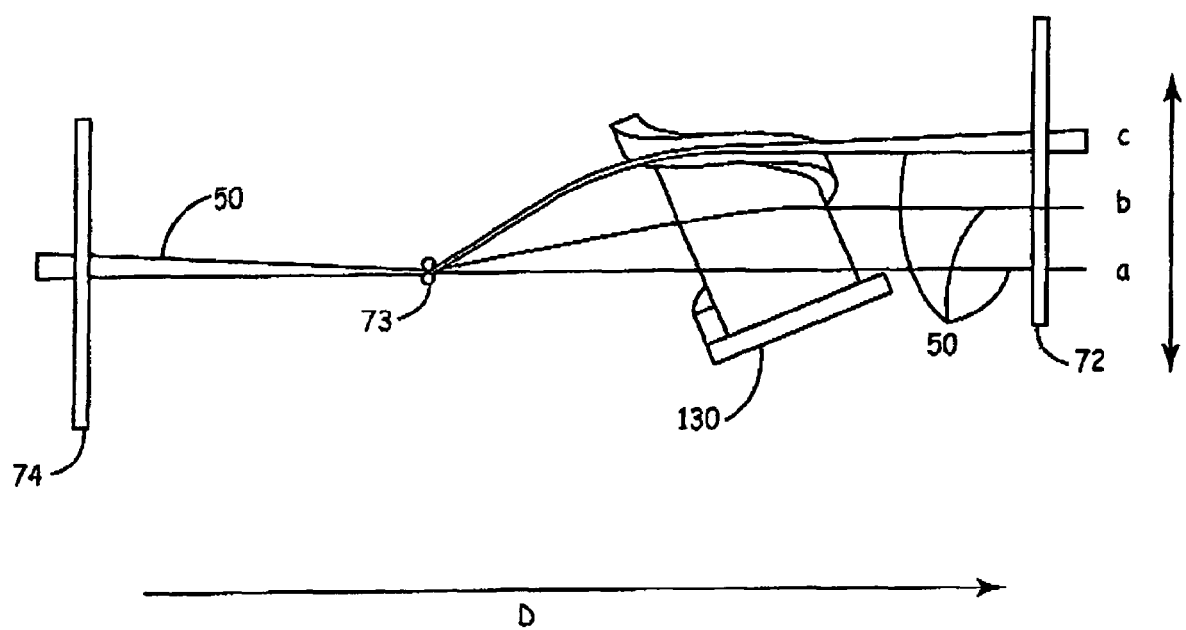
FIG. 22 illustrates a top view showing end positions of an elastic ribbon on the combining roll due to rotation of the diverter in accordance with an embodiment.
Figure 23:
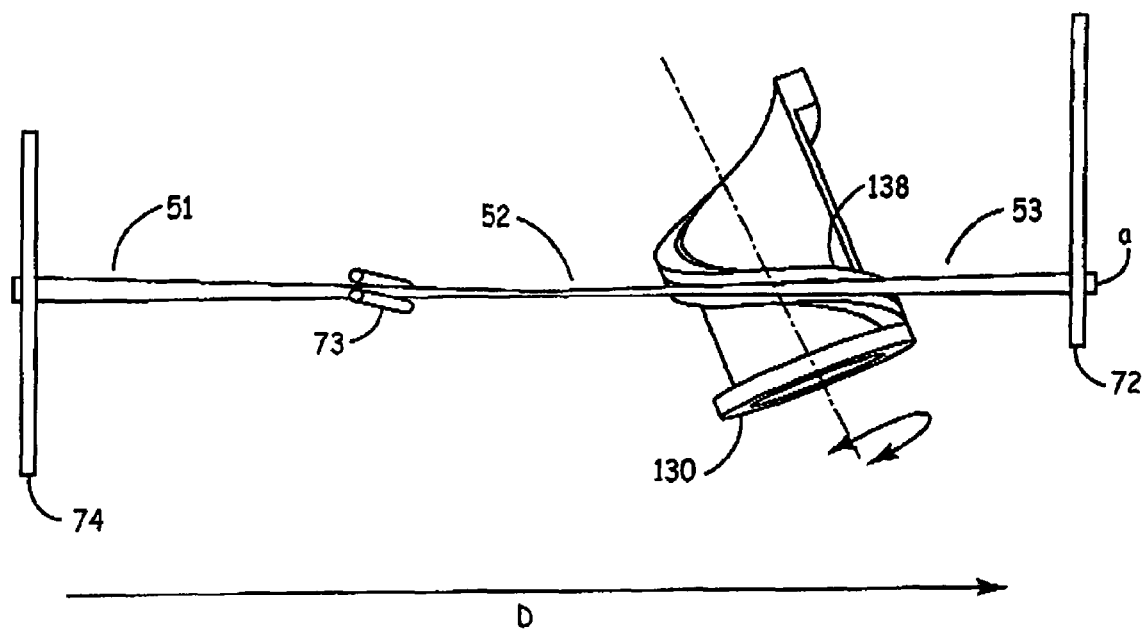
FIG. 23 illustrates a top view showing orientations of an elastic ribbon along an elastics station in accordance with an embodiment.

FIG. 22 illustrates the cross machine movement range available to the elastic member 50 by rotating the diverter about 360 degrees or less. The direction of movement of the elastic member 50 is shown by direction D. As shown, the elastic member 50 may be laid in positions a, b, or c by adjusting the rotation of the diverter 130. The elastic member 50 may further be laid intermediate to positions a, b, and c. FIG. 23 illustrates the elastic member 50 being laid in position a of FIG. 22. FIG. 23 further illustrates the orientation of an elastic ribbon as the elastic member 50 during laying of the elastic member 50. The elastic ribbon 50 has a length, a width, and a depth or thickness. The length is generally continuously fed to the diverter 130 for application to the continuous web 20. The depth or thickness of the elastic ribbon 50 may be varied depending on the design of the diaper. The width of the ribbon forms the extent of the elastic ribbon 20 between longitudinal edges of the diaper. Generally, the width is laid in a manner such that the elastic ribbon 50 is not twisted as applied to the diaper. As shown, between the first positioning member 74 and the second positioning member 72, the ribbon has a horizontal orientation wherein the width of the ribbon extends horizontally, shown at 51. Between second positioning member 73 and the diverter 130, the ribbon has a generally vertical orientation wherein the width of the ribbon extends vertically for receipt by the groove 138 of the diverter 130, shown at 52. Thus, the ribbon travels through the groove in a direction generally perpendicular to that of the axis of rotation 1600 of the combining roll 160. Such orientation prevents the ribbon from being wrinkled or bunched during cross machine direction movement due to the oscillation of the diverter 130. Between the diverter 130 and the third positioning member 72, the ribbon has a generally horizontal orientation wherein the width of the ribbon extends horizontally, shown at 53. Generally, it is desirable to place the ribbon on the continuous web 20 so that the surfaces of the ribbon and the continuous web roughly match. As shown in the embodiment of FIG. 23, the first and second positioning members 74, 72 may each comprise at least one rotating turning bar. In some embodiments, the first positioning member 74 and the second positioning member 72 may not be included. Thus, the ribbon may be fed directly to the diverter 130 in an orientation corresponding to the groove 138 of the diverter 130

Figure 24:
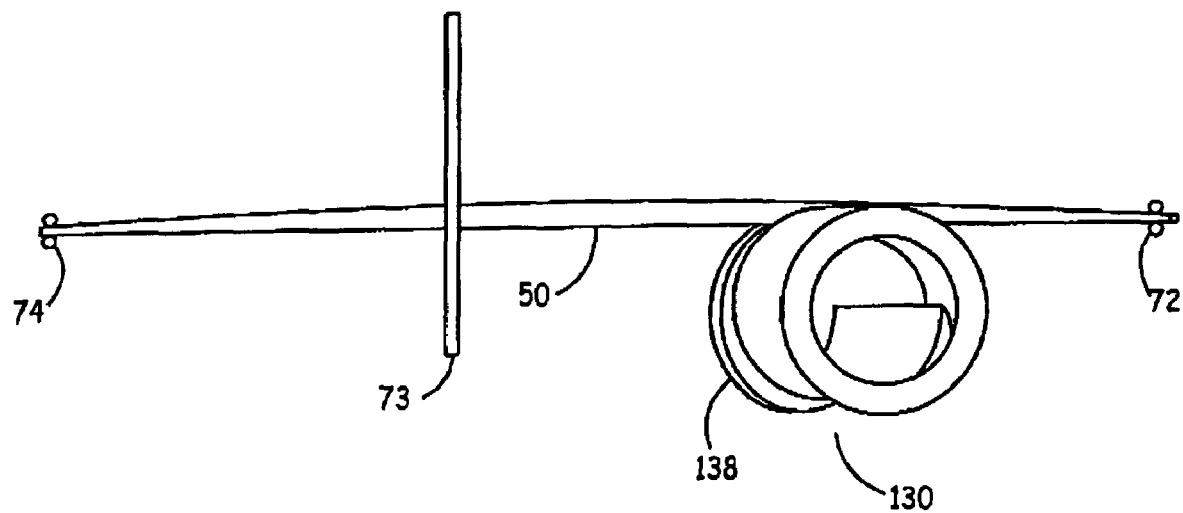
FIG. 24 illustrates a side view showing orientations of an elastic ribbon as received in a groove of a diverter in accordance with an embodiment.

FIG. 24 illustrates the positioning of the elastic member 50, such as an elastic ribbon. As previously described, first, second, and third positioning members 74, 73, and 72, respectively, are provided for positioning the elastic member 50. The elastic member 50 is generally oriented in the direction of the depth of the groove 138 of the diverter 130 by using the second positioning member 73. The ribbon 50 then passes through the groove 138, rather than wrapping around the bottom of the groove 138. Wrapping of the ribbon 50 around the diverter 130 could result in wrinkling or deformation of the ribbon 50. In the embodiment of FIG. 23, the first positioning member 74 comprises a pair of idlers and the second and third positioning members, 73 and 72, respectively, each comprise a pair of rotating turning bars.

Figure 25:
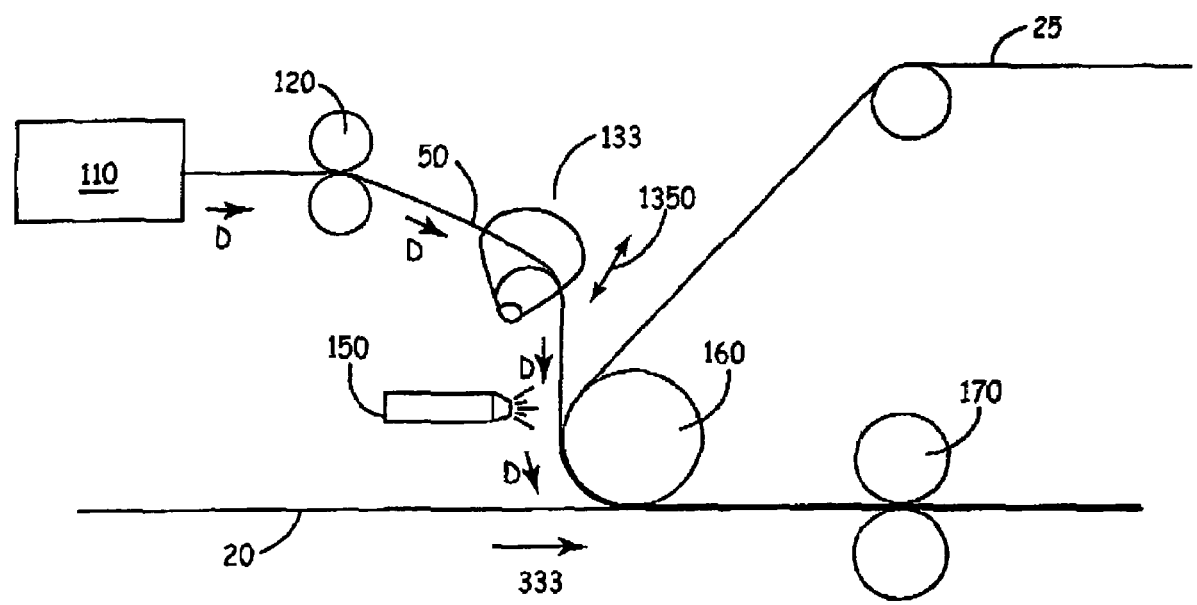
FIG. 25 illustrates a schematic view of an apparatus setup including a generally conical diverter for laying an elastic member in accordance with an embodiment.

FIGS. 25-29 illustrate an elastics station. The elastics station comprises a generally conical diverter 133 and a combining roll 160. FIG. 25 illustrates another embodiment of an apparatus setup for laying the elastic member. As shown, a continuous web 20 is fed through the elastics station in direction 333. The elastics station comprises a generally conical diverter 133 and a combining roll 160. The continuous web 20 is directed beneath the combining roll 160. A coupling mechanism 150, such as a glue gun or other suitable device, may also be provided for applying a coupling material to couple the elastic member 50 to the second web 25 and then to the continuous web 20. The coupling mechanism 150 may be provided proximate the elastic member 50 at any suitable location and is shown generally proximate the combining roll 160.

An elastic member 50 is fed to the elastics station. A supply 110 of elastic member 50 may be fed through an elastic metering system 120, which dispenses the material. The elastic member may comprise an elastic strand, an elastic ribbon, etc. In some embodiments, more than one elastic member may be fed to the elastics station. The elastics member 50 is diverted along the diverter 133 in the cross-machine direction 1350 to determine the elastic profile laid on the continuous web 20. The elastic member 50 is directed in the direction D around the combining roll 160 to a position over the continuous web 20. A second web 25 may also be fed around the combining roll 160 to a position proximate the elastic member 50. A supply 110 of elastic member 50 may be fed through an elastic metering system 120. Similarly, a metering station may be provided for the continuous web 20. The combining roll 160 may be chilled to advance settling of an adhesive used to couple the elastic member 50 to the continuous web 20. After the elastic member 50 has been laid on the continuous web 20, the web may be fed to a chill roll 170. The chill roll 170 adheres a second web 25 to the continuous web 20 proximate the elastic member 50. The elastic member 50 is thus captured between the continuous web 20 and the second web 25. The second web 25 may also set the adhesive (applied by coupling mechanism 150), hold the elastic profile, and return force if the elastic member has stretch.

Figure 26:
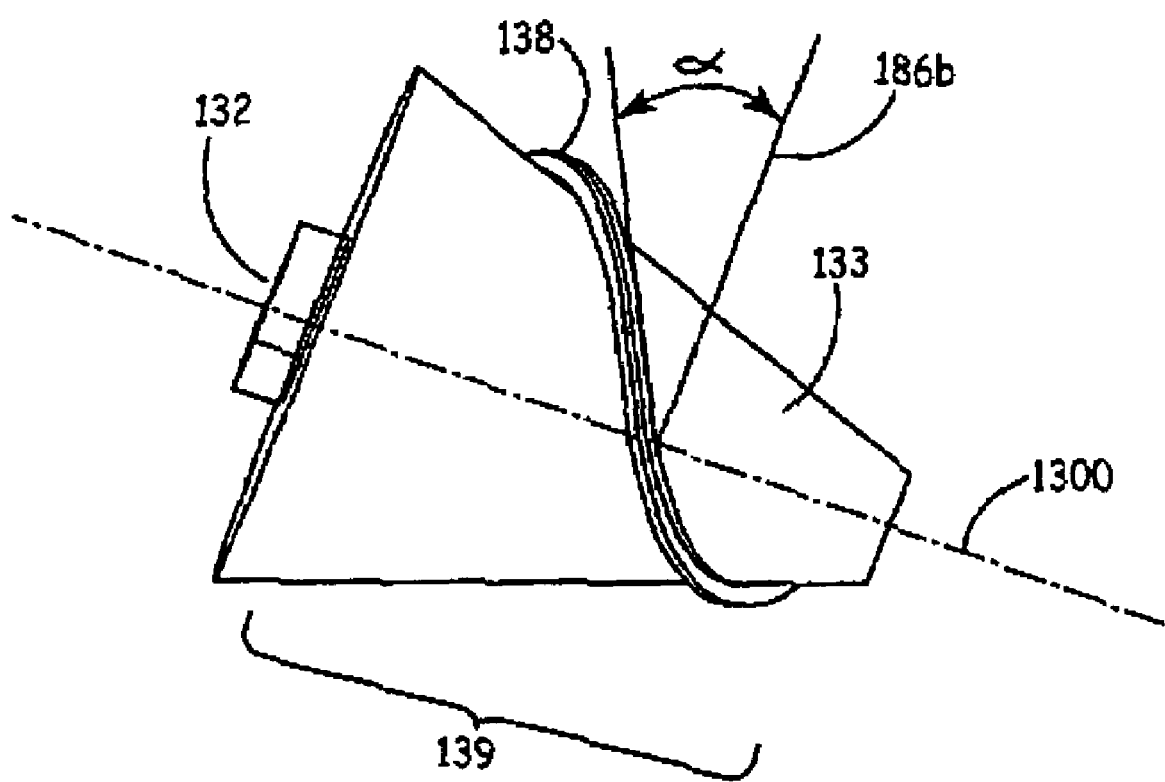
FIG. 26 illustrates a generally conical diverter in accordance with an embodiment.

FIG. 26 more closely illustrates the generally conical diverter 133. Using a generally conical diverter 133, a constant distance 147 is achieved between the diverter 130 and the combining roll 160 (see FIG. 27). Further, using a generally conical diverter 133 positions the adjacent sides of the diverter and the combining roll in a generally parallel orientation, which provides for a shorter distance between the two rolls. This may be useful when longer diverters are used. The diverter 133 has a generally conical shape and may be relatively light weight.

The generally conical diverter 133 comprises at least one groove 138 wrapping spirally therearound. The groove 138 may be formed in any suitable manner. In one embodiment, the groove 138 comprises a raised section on the diverter 133. In another embodiment, the groove 138 may comprise a cut in the surface of the diverter 133. In another embodiment, the groove 138 may comprise a cut on a raised section of the diverter 133. The groove 138 has a pitch 139. The pitch 139 is the axial length that the groove 138 travels to make one complete revolution. The pitch 139 can be determined and referenced via its angle α relative to a line 138b drawn generally perpendicular to the central axis 1300 of the diverter 133. As discussed more fully below, the pitch 139 of the groove 138 contributes to the set up of the elastics station. The pitch 139 may be set at any suitable length. In order to lay more than one elastic member 50, more than one groove 138 may be provided on the diverter 133. For example, generally parallel grooves 138 may be provided spaced apart from one another on the diverter 133 to lay generally parallel elastic members 50 on the continuous web 20. Alternatively, two grooves may be provided on the diverter in opposite directions to lay elastic members 50 on opposite sides of the continuous web 20. For such embodiments, the pitch of the grooves may be longer or the diverter 130 may be wider.

The groove 138 includes a receiving portion for receiving the elastic member. As shown, the receiving portion 137 is formed by an open surface on the outer side relative to the axis of rotation of the diverter 133. The elastic member, as received by the groove 138, conforms to the bottom of the groove 138. The diverter 133 may be manufactured of a sufficiently light weight material to permit rapid servo motor response and duty cycle. Mounting of the diverter 133 to a motor, such as a servo motor, may be done in any suitable manner. For example, a hole may be machined in a face plate 132 of the diverter 133 concentric to the rotational central axis 1300 of the diverter 133. Further, a second motor may be provided on the end opposite to the first motor. Alternatively, a bearing supporting the weight of the diverter 133 may be provided at the end opposite to the first motor.

Figure 27:
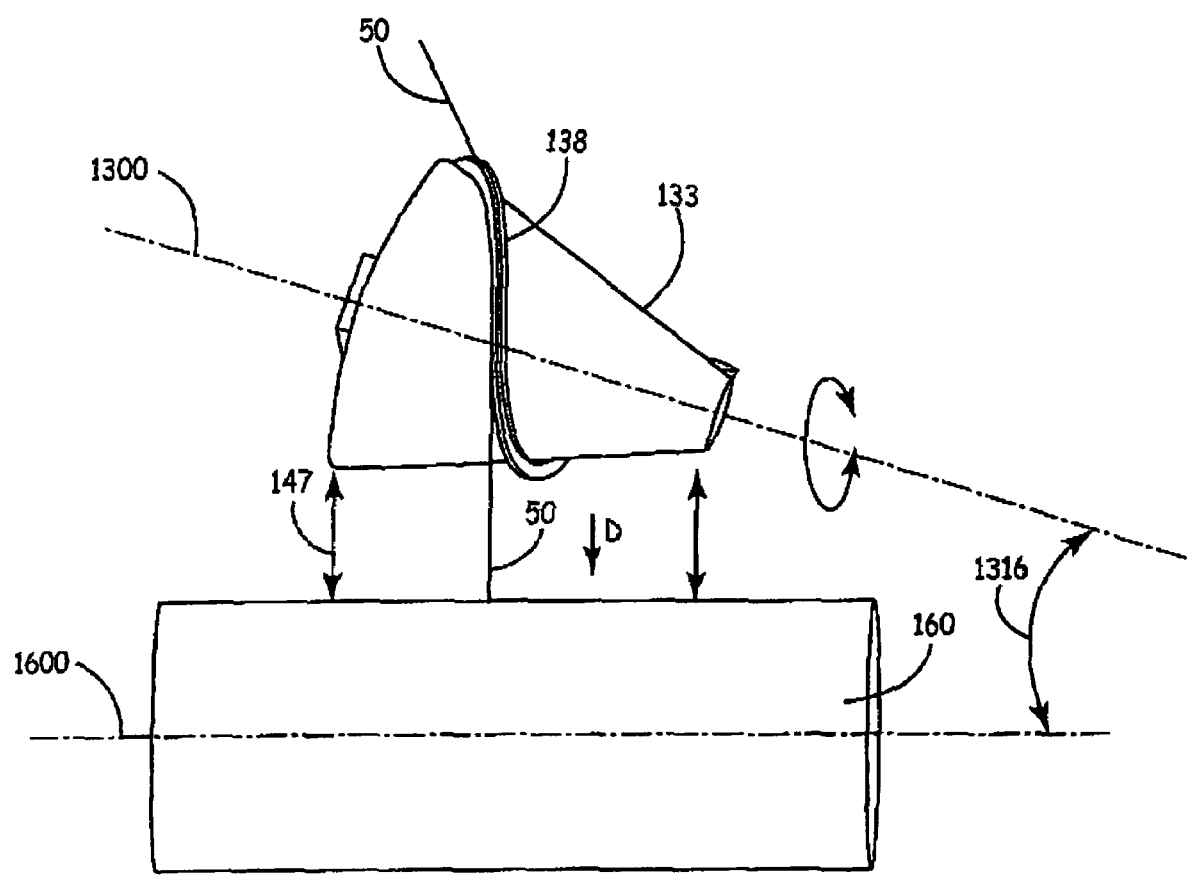
FIG. 27 illustrates a side view showing the angle between the axis of rotation of the generally conical diverter and the axis of rotation of the combining roll in accordance with an embodiment.
Figure 28:
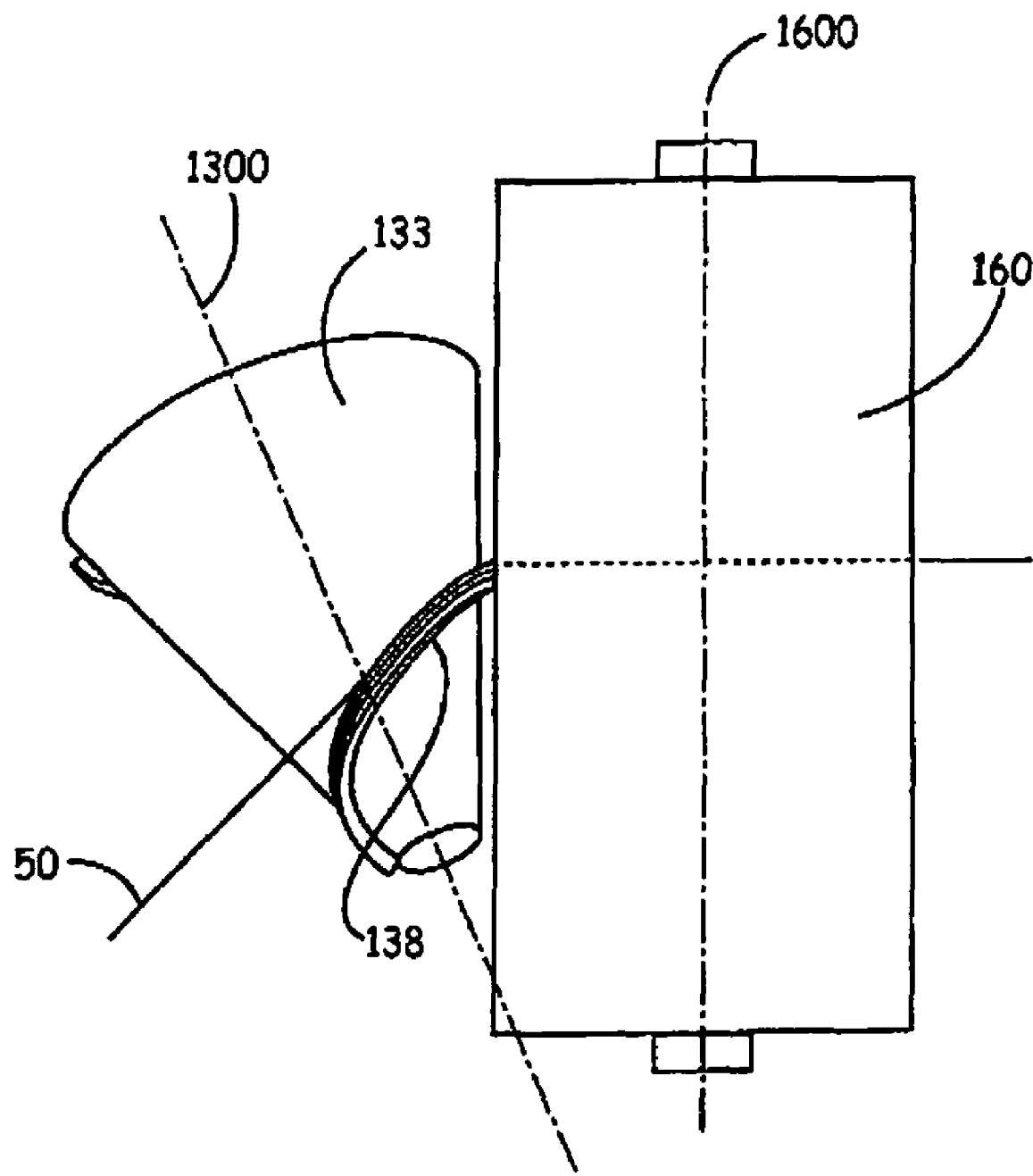
FIG. 28 illustrates a top view of the generally conical diverter and combining roll of FIG. 27.
Figure 29:
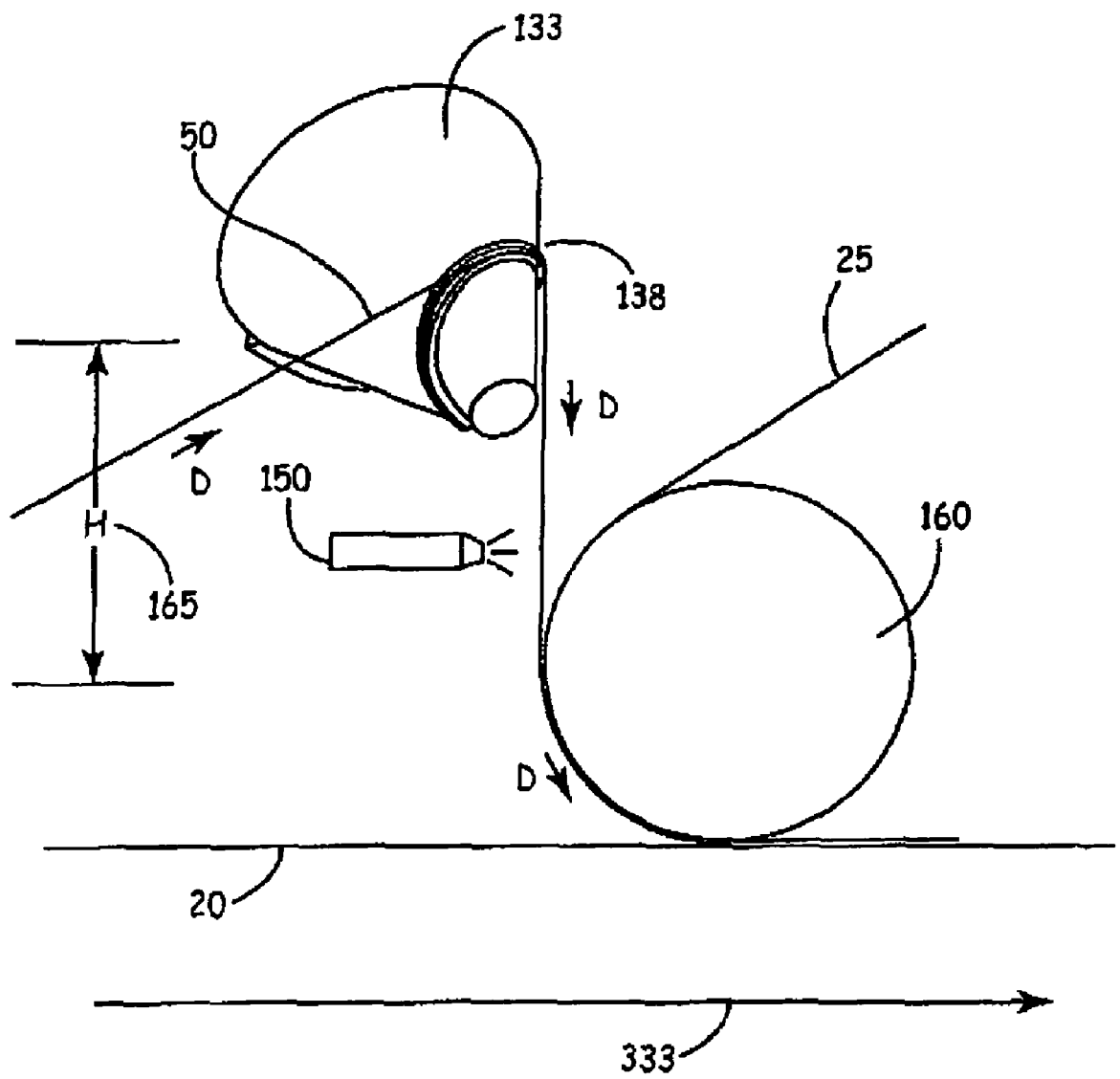
FIG. 29 illustrates a schematic view of an elastics station including a generally conical diverter and a combining roll in accordance with an embodiment.

FIGS. 27-29 show the elastics station comprising a conical diverter 133 and a combining roll 160. In the embodiment of FIG. 27, the generally conical diverter 133 and the combining roll 160 have generally nonparallel axes of rotation 1300 and 1600 respectively. The angle 1316 of the axis of rotation 1300 of the diverter 133 relative to the axis of rotation 1600 of the combining roll 160 is set to create a generally perpendicular angle between the exit point of the elastic member 50 from the groove 138 of the diverter 133 to the combining roll 160. This arrangement provides a smooth open channel for the elastic member to exit. As shown, the elastic member 50 travels in the direction D from the conical diverter 133 to the combining roll 160. Using a generally conical diverter 133, a constant distance 147 is achieved between the diverter 133 and the combining roll 160. The angle 1316 of the axis of rotation 1600 of the combining roll 160 relative the axis of rotation 1300 of the diverter 133 is thus related to the pitch of the groove 138. The pitch of the groove 138 is a function of the cross machine movement the elastic member 50 travels for one rotation of the diverter 133. Because, in this embodiment, the diverter 133 is set at an angle to create a generally perpendicular exit opening of the groove to the combining roll 160, some of the cross machine movement may be lost. More specifically, diverters 133 containing longer pitches require the set-up angle to be steeper to create the generally perpendicular portion of the groove 138 where the elastic member exits to the combining roll 160. This steeper angle reduces the amount of actual cross machine movement compared to the pitch of the groove 138 on the diverter 130. Clockwise and counter clockwise rotation oscillations of the diverter 133 divert the elastic in the cross machine direction.

The rotation of the diverter 133 and the oscillation of the rotation of the diverter 133 generally sets the elastic profile. Oscillation of rotation of the diverter 133 in the clockwise and counterclockwise directions move the exit point of the elastic member 50 from the groove 138 on the diverter 133. The degree of rotation and the speed of rotation impact the elastic profile. Further, the speed of the continuous web 20 can impact the elastic profile. More specifically, the speed of the continuous web 20 can affect the speed at which it pulls the elastic member 50 away from the diverter 133. Thus, a slower carrier web speed generally will result in a steeper travel path of the elastic member 50. As previously discussed, as the diverter 133 rotates, an elastic path angle is created between the contact point of the elastic member 50 with the combining roll 160 and the exit point of the elastic member 50 from the groove 138 of the diverter 133. This elastic path angle automatically transitions such that the elastic member 50 is drawn tangent to the diverter 133, thus moving the contact point of the elastic member 50 with the combining roll 160, thereby moving the elastic profile. Thus, movement of the elastic profile starts when the diverter 133 is rotated a degree of rotation. This moves the exit point on the diverter 133 and the elastic profile curves until the elastic path is tangent to the diverter 133. Thus, faster rotation movement and a larger degree of rotation will result in stepper profiles and faster movements.

As seen in FIG. 27, while the axes of rotation 1300, 1600 of the diverter 133 and the combining roll 160 are generally nonparallel, outer surfaces of the diverter 133 and the combining roll 160 are generally parallel. Thus, a consistent cross machine travel path is provided through adhesive application 150 (see FIG. 29). A smooth travel path for the elastic member 50 to exit the diverter 133 and travel to the combining roll 160 is further provided.

The generally conical diverter 133 and the combining roll 160 are set apart at a height 165, shown in FIG. 29. The height 165 represents the distance between where the elastic member exits the diverter 133 and where the elastic member contacts the combining roll 160. The speed at which the elastic member 50 travels in the cross machine direction is related to the distance represented by the height 165. For example, a longer distance 165 results in a slower response time. When the diverter 133 rotates, the elastic member 50 is pulled along an at angle 1316 (see FIG. 27) between the diverter 133 and the combining roll 160. The angle 1316 is the angle between the axis of rotation 1300 of the diverter 133 and the axis of rotation of the combining roll 160. The elastic automatically travels in a generally vertical path exiting the diverter 133 to the combining roll 160. Thus, the path the elastic member 50 travels initially is angled as the diverter 130 rotates. The angle of the elastic member 50 to the diverter 130 as the elastic member 50 exits the diverter may be referred to as the elastic path angle. This angle automatically transitions to be perpendicular with the diverter 130 such that the elastic path becomes tangent to the diverter 130 as the elastic member 50 automatically travels in the generally vertical path exiting the diverter 130 to the combining roll 160. A longer distance of the height 165 creates a shallower elastic path angle resulting in slower cross machine travel speed. Correspondingly, a shorter distance of the height 165 creates a steeper elastic path angle, resulting in faster cross machine travel speed. Any suitable height 165 may be used, for example ranging from approximately 10 mm to approximately 300 mm, or suitable heights outside this range. In one embodiment, the height 165 is approximately 70 mm. The degree of elastic wrap around the diverter 133 may be referred to as the wrap angle 146. In one embodiment, the method utilizes an approximately 90 degree wrap angle 146. This angle may be reduced down to approximately 10 degrees or increased to multiple revolutions around the diverter 133.

Turning to FIG. 29, the elastic member 50 is travels in the direction D to the conical diverter 133, where it is fed through the groove 138 and exits towards the combining roll 160. The conical diverter 133 and the combining roll 160 are separated by a height 165. A coupling mechanism 150 may be provided for applying an adhesive or other coupling material to the elastic member for coupling to second web 25 and then to the continuous web 20. The continuous web 20 is traveling in direction 333. The elastic member 50 meets the continuous web 20 at the combining roll 160. A second web 25 may be fed to the continuous web 20 proximate the elastic member 50.

Figure 30:
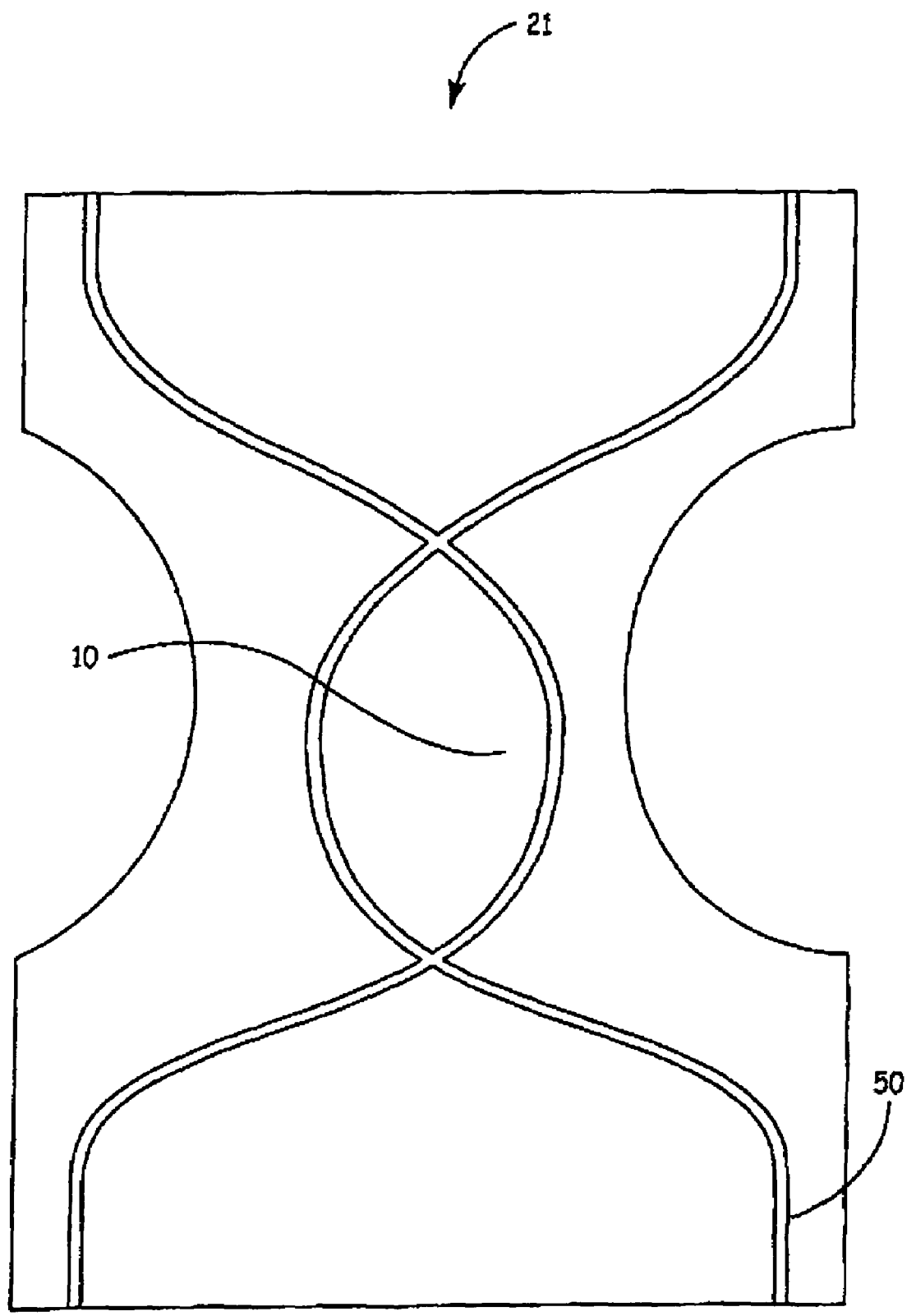
FIG. 30 illustrates a top view of an article having an elastic profile wherein each extent of elastic comprises two elastic members provided side-by-side in accordance with an embodiment.

FIG. 1 illustrates an article 21 having an elastic members 50 generally parallel to the side edges 40 of the article 21. FIG. 30 illustrates an article 21 having an elastic profile 10 diverting into a much larger cross machine direction. FIG. 30 further illustrates an elastic profile 10 wherein each extent of elastic comprises two elastic members 50 provided side by side. In alternative embodiments, more than two elastic members 50 may be used.

The elastic members may be secured to the article in an elastically contractible condition so that, in a normally unrestrained configuration, the elastic members effectively contract or gather portions of the diaper. The elastic members can be secured in an elastically contractible condition in any suitable manner. For example, the elastic members can be stretched and secured while the article is in an uncontracted condition. Alternatively, the article can be contracted, for example, by pleating, and the elastic members can be secured and connected to the article while the elastic members are in their unrelaxed or unstretched condition. Any other suitable method also may be used.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm.

All documents cited in the Detailed Description of the invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and the scope of the invention. It is therefore intended to cover in the appended claims all such changes and modifications that are within the scope of this invention.

What is claimed is:

1. An apparatus for laying an elastic member on a continuous web moving in a machine direction, the apparatus comprising:
   a diverter having a groove and an axis of rotation, the groove having a pitch corresponding to an axial length of the groove as it wraps once around an outer surface of the diverter, the groove being configured for receiving the elastic member and for directing the elastic member out of an exit point of the groove, the diverter being configured for oscillating rotation, wherein rotation of the diverter moves the exit point in a cross machine direction;
   a combining roll having an axis of rotation, the combining roll being configured for receiving the elastic member from the diverter and combining the elastic member with the continuous web;
   wherein the axis of rotation of the diverter is positioned at a generally nonparallel angle relative to the axis of rotation of the combining roll such that an elastic member travels from the exit point of the groove of the diverter to the combining roll on a path that is generally perpendicular to the axis of rotation of the combining roll; and
   wherein the apparatus is configured to vary an elastic profile of the elastic member on the continuous web by oscillating a rotation of the diverter.

2. The apparatus of claim 1, wherein a shape of the outer surface of the diverter is generally cylindrical.

3. The apparatus of claim 2, wherein openings are provided in the diverter for reducing inertia of the diverter.

4. The apparatus of claim 1, wherein a shape of the outer surface of the diverter is generally conical.

5. The apparatus of claim 4, wherein the diverter and the combining roll are positioned such that the outer surface of the diverter is generally parallel to an outer surface of the combining roll.

6. The apparatus of claim 1, wherein the angle is based on the pitch of the groove.

7. The apparatus of claim 1, further comprising a second groove on the diverter, wherein the second groove is configured for receiving an elastic member and for directing the elastic member out of an exit point of the second groove.

8. The apparatus of claim 7, wherein at least a portion of the second groove is generally parallel to at least a portion of the first groove.

9. The apparatus of claim 7, wherein the second groove is opposite to the first groove.

10. The apparatus of claim 1, wherein the groove is included on a raised section on the diverter.

11. The apparatus of claim 1, wherein the groove is cut into the outer surface of the diverter.

12. The apparatus of claim 1, wherein the groove wraps continuously around the outer surface of the diverter.

13. The apparatus of claim 1, further comprising a coupling mechanism for coupling the elastic member to the continuous web.

14. The apparatus of claim 1, further comprising a first positioning member for changing the orientation of an elastic member from a generally horizontal orientation to a generally vertical orientation or from a generally vertical orientation to a generally horizontal orientation, the first positioning member being provided upstream from the diverter or downstream from the diverter.

15. The apparatus of claim 14, further comprising a second positioning member, wherein the first positioning member is positioned upstream of the diverter and orients the elastic member in to be received by the groove and wherein the second positioning member is positioned between the diverter and the combining roll and orients the elastic member to be received by the combining roll for combining the elastic member with the continuous web.

16. The apparatus of claim 1, wherein the combining roll is further configured to receive a second web such that the second web is layered over the continuous web and the elastic member.

17. The apparatus of claim 16, further comprising a chill roll downstream of the combining roll.

18. The apparatus of claim 1, wherein rotating the diverter in a clockwise direction moves the exit point a first way in a cross machine direction and rotating the diverter in a counterclockwise direction moves the exit point a second way in a cross machine direction.

19. The apparatus of claim 1, wherein rotating the diverter imparts a curvature to the elastic profile.

20. The apparatus of claim 19, wherein rotating the diverter at a faster speed imparts a steeper curvature to the elastic profile and rotating the diverter at a slower speed imparts a shallower curvature to the elastic profile.

21. The apparatus of claim 1, further comprising a servo motor for driving the diverter, and wherein the elastic profile may be modified by modifying instructions to the servo motor regarding oscillation of the diverter.

22. An apparatus for laying an elastic member on a continuous web moving in a machine direction, the apparatus comprising:
a diverter having a groove and an axis of rotation, the groove having a pitch corresponding to an axial length of the groove as it wraps once around an outer surface of the diverter, the groove being configured for receiving the elastic member and for directing the elastic member out of an exit point of the groove, the diverter being configured for oscillating rotation, wherein rotation of the diverter moves the exit point in a cross machine direction;
a combining roll having an axis of rotation, the combining roll being configured for receiving the elastic member form the diverter and combining the elastic member with the continuous web;
a first positioning member positioned upstream of the diverter, wherein the first positioning member holds the elastic member in a first orientation;
a second positioning member positioned between the first positioning member and the diverter, wherein the second positioning member orients the elastic member to correspond generally with orientation of the groove; and
a third positioning member positioned between the diverter and the combining roll, wherein the third positioning member orients the elastic member to generally correspond with orientation of the continuous web;
wherein the axis of rotation of the diverter is positioned at a generally nonparallel angle relative to the axis of rotation of the combining roll such that an elastic member travels from the exit point of the groove of the diverter to the combining roll on a path that is generally perpendicular to the axis of rotation of the combining roll; and
wherein the apparatus is configured to vary an elastic profile of the elastic member on the continuous web by oscillating a rotation of the diverter, 23. The apparatus of claim 22, wherein the first positioning member comprises a set of idlers, the second positioning member comprises a set of rotating turning bars, and the third positioning member comprises a set of rotating turning bars.

24. An apparatus for laying an elastic member on a continuous web, the apparatus comprising:
a generally conical diverter having a generally conical outer surface, a groove on the conical outer surface, and an axis of rotation, the groove having a pitch corresponding to an axial length of the groove as it wraps once around an outer surface of the diverter, the groove being configured for receiving the elastic member and for directing the elastic member out of an exit point of the groove, the diverter being configured for oscillating rotation, wherein rotation of the diverter moves the exit point in a cross machine direction;
a combining roll having an axis of rotation, the combining roll being configured for receiving the elastic member from the diverter and combining the elastic member with the continuous web;
wherein the axis of rotation of the diverter is positioned at a generally nonparallel angle relative to the axis of rotation of the combining roll such that an elastic member travels from the exit point of the groove of the diverter to the combining roll on a path that is generally perpendicular to the axis of rotation of the combining roll and wherein an outer surface of the generally conical diverter is generally parallel to an outer surface of the combining roll; and
wherein the apparatus is configured to vary by oscillating a rotation of the diverter.

25. A method for laying an elastic member on a continuous web moving in a machine direction, the method comprising:
providing a diverter having a groove and an axis of rotation, the groove having a pitch corresponding to an axial length of the groove as it wraps once around an outer surface of the diverter, the groove being configured for receiving the elastic member and for directing the elastic member out of an exit point of the groove, the diverter being configured for oscillating rotation, wherein rotation of the diverter moves the exit point in a cross machine direction;
providing a combining roll having an axis of rotation, the combining roll being configured for receiving the elastic member from the diverter and combining the elastic member with the continuous web;
directing the elastic member into the groove;
oscillating a rotation of the diverter to move the exit point in a cross machine direction while feeding the elastic member through the groove;
directing the elastic member from the exit point to the combining roll on a path that is generally perpendicular to the axis of rotation of the combining roll; and
combining the elastic member with the continuous web using the combining roll.

26. The method of claim 25, wherein providing a diverter further comprises providing a second groove on the diverter, wherein the second groove is configured for receiving an elastic member and for directing the elastic member out of an exit point of the second groove, the method further comprising directing a second elastic member into the second groove and directing the second elastic member from the exit point of the second groove on a path that is generally perpendicular to the axis of rotation of the combining roll.

27. The method of claim 25, further comprising applying a coupling material to the elastic member before combining the elastic member with the continuous web.

28. The method of claim 25, further comprising changing the orientation of the elastic member from a first orientation to an orientation for receipt by the groove.

29. The method of claim 27, wherein oscillating a rotation of the diverter comprises rotating the diverter in a clockwise direction to move the exit point a first way in a cross machine direction or rotating the diverter in a counterclockwise direction to move the exit point a second way in a cross machine direction.

30. The method of claim 27, wherein oscillating a rotation of the diverter imparts a curvature to the elastic profile.

31. The method of claim 30, wherein oscillating a rotation of the diverter at a faster speed imparts a steeper curvature to the elastic profile and rotating the diverter at a slower speed imparts a shallower curvature to the elastic profile.

32. A diverter for laying an elastic member on a continuous web moving in a machine direction, the diverter comprising:

a generally conical diverter having a generally conical outer surface and a groove on the conical outer surface, the groove having a pitch corresponding to an axial length of the groove as it wraps once around an outer surface of the diverter, the groove being configured for receiving the elastic member and for directing the elastic member out of an exit point of the groove, the diverter being configured for oscillating rotation, wherein rotation of the diverter moves the exit point in a cross machine direction.

* * * * *